(12) United States Patent
Ryan

(10) Patent No.: US 7,507,215 B2
(45) Date of Patent: Mar. 24, 2009

(54) ORTHOTIC BRACE

(75) Inventor: Jeff Ryan, Willow Spring, NC (US)

(73) Assignee: JRI Development Group, LLC, Mooresville, NC (US)

( * ) Notice: Subject to any disclaimer, the term of this patent is extended or adjusted under 35 U.S.C. 154(b) by 211 days.

(21) Appl. No.: 11/456,448

(22) Filed: Jul. 10, 2006

(65) Prior Publication Data

US 2007/0010772 A1    Jan. 11, 2007

Related U.S. Application Data

(60) Provisional application No. 60/697,426, filed on Jul. 8, 2005, provisional application No. 60/697,513, filed on Jul. 8, 2005, provisional application No. 60/698,157, filed on Jul. 11, 2005.

(51) Int. Cl.
*A61F 5/00* (2006.01)
(52) U.S. Cl. .............................. 602/23; 602/16; 602/26
(58) Field of Classification Search .................. 602/27, 602/23, 26, 24, 28, 16, 6, 62; 128/882
See application file for complete search history.

(56) References Cited

U.S. PATENT DOCUMENTS

| | | | |
|---|---|---|---|
| 2,638,605 A | 5/1953 | Johnson | |
| 2,859,451 A | 11/1958 | Mauch | |
| 2,877,033 A | 3/1959 | Koetke | |
| 3,316,558 A | 5/1967 | Mortensen | |
| 3,683,897 A | 8/1972 | Shield et al. | |
| 3,799,159 A | 3/1974 | Scott | |
| 3,823,424 A | 7/1974 | May | |
| 3,826,251 A | 7/1974 | Ross | |
| 3,885,252 A | 5/1975 | Nakajima | |
| 3,901,223 A * | 8/1975 | May .......................... | 602/16 |
| 3,969,773 A | 7/1976 | Menschik | |
| 3,976,057 A | 8/1976 | Barclay | |
| 3,985,127 A | 10/1976 | Volkov et al. | |
| 4,005,496 A | 2/1977 | Wilkes | |
| 4,064,569 A | 12/1977 | Campbell | |
| 4,145,766 A | 3/1979 | May | |
| 4,209,860 A | 7/1980 | Graupe | |
| 4,245,629 A | 1/1981 | Cummins | |
| 4,351,070 A | 9/1982 | Blatchford | |
| 4,361,142 A | 11/1982 | Lewis et al. | |
| 4,428,369 A | 1/1984 | Peckham et al. | |
| 4,463,751 A | 8/1984 | Bledsoe | |
| 4,523,585 A | 6/1985 | Lamb et al. | |
| 4,655,201 A | 4/1987 | Pirmantgen | |

(Continued)

FOREIGN PATENT DOCUMENTS

EP    0 297 766 B1    4/1992

(Continued)

*Primary Examiner*—Patricia M Bianco
*Assistant Examiner*—Ophelia Hawthorne
(74) *Attorney, Agent, or Firm*—Hammer & Associates, P.C.

(57) ABSTRACT

An articulated assembly for replacing or supporting a joint between two limbs of an animal. In one embodiment, the present invention relates to an orthotic knee brace for supporting a human knee. The knee brace includes an upper leg attachment and a lower leg attachment which are interconnected with a hinge and a damper. In some embodiments, the hinge is a four bar linkage and the damper is a hydraulic shock absorber.

24 Claims, 23 Drawing Sheets

U.S. PATENT DOCUMENTS

| | | | |
|---|---|---|---|
| 4,671,257 A | 6/1987 | Kaiser et al. | |
| 4,685,927 A | 8/1987 | Haupt | |
| 4,699,129 A | 10/1987 | Aaserude et al. | |
| 4,715,363 A | 12/1987 | Detty | |
| 4,723,539 A | 2/1988 | Townsend | |
| 4,732,143 A | 3/1988 | Kausek et al. | |
| 4,790,299 A | 12/1988 | Marquette | |
| 4,801,138 A | 1/1989 | Airy et al. | |
| 4,821,707 A | 4/1989 | Audette | |
| 4,856,501 A | 8/1989 | Castillo et al. | |
| 4,865,606 A | 9/1989 | Rehder | |
| 4,886,054 A | 12/1989 | Castillo et al. | |
| 4,890,607 A | 1/1990 | Townsend | |
| 4,911,177 A | 3/1990 | Lamb et al. | |
| 4,911,709 A | 3/1990 | Marlow et al. | |
| 4,919,119 A | 4/1990 | Jonsson et al. | |
| 4,940,044 A | 7/1990 | Castillo | |
| 4,940,045 A | 7/1990 | Cromartie | |
| 4,955,369 A | 9/1990 | Bledsoe et al. | |
| 4,961,416 A | 10/1990 | Moore et al. | |
| 5,000,169 A | 3/1991 | Swicegood et al. | |
| RE33,621 E | 6/1991 | Lamb et al. | |
| 5,022,391 A | 6/1991 | Weidenburner | |
| D318,736 S | 7/1991 | Castillo | |
| 5,038,765 A | 8/1991 | Young et al. | |
| 5,042,464 A | 8/1991 | Skwor et al. | |
| 5,052,379 A | 10/1991 | Airy et al. | |
| 5,086,760 A | 2/1992 | Neumann et al. | |
| 5,103,811 A | 4/1992 | Crupi | |
| 5,116,296 A | 5/1992 | Watkins et al. | |
| 5,117,814 A | 6/1992 | Luttrell et al. | |
| 5,135,469 A | 8/1992 | Castillo | |
| 5,168,865 A | 12/1992 | Radcliffe et al. | |
| 5,215,508 A | 6/1993 | Bastow | |
| 5,230,697 A | 7/1993 | Castillo et al. | |
| 5,259,832 A | 11/1993 | Townsend et al. | |
| 5,286,242 A | 2/1994 | Johnston | |
| 5,288,287 A | 2/1994 | Castillo et al. | |
| 5,330,418 A | 7/1994 | Townsend et al. | |
| 5,337,737 A | 8/1994 | Rubin et al. | |
| 5,356,370 A | 10/1994 | Fleming | |
| 5,372,572 A | 12/1994 | Tamagni | |
| 5,383,939 A | 1/1995 | James | |
| D357,070 S | 4/1995 | Castillo | |
| 5,409,449 A | 4/1995 | Nebolon | |
| 5,410,472 A | 4/1995 | Anderson | |
| 5,413,611 A | 5/1995 | Haslam, II et al. | |
| 5,443,444 A | 8/1995 | Pruyssers | |
| 5,443,521 A | 8/1995 | Knoth et al. | |
| 5,472,410 A | 12/1995 | Hamersly | |
| 5,472,412 A | 12/1995 | Knoth | |
| 5,476,441 A | 12/1995 | Durfee et al. | |
| 5,490,822 A | 2/1996 | Biedermann | |
| 5,547,464 A | 8/1996 | Luttrell et al. | |
| 5,571,205 A | 11/1996 | James | |
| 5,586,970 A | 12/1996 | Morris et al. | |
| 5,598,849 A | 2/1997 | Browne | |
| 5,611,774 A | 3/1997 | Postelmans | |
| 5,624,389 A | 4/1997 | Zepf | |
| 5,658,243 A | 8/1997 | Miller et al. | |
| 5,658,244 A | 8/1997 | Townsend et al. | |
| 5,672,152 A | 9/1997 | Mason et al. | |
| 5,683,336 A | 11/1997 | Pape | |
| 5,683,353 A | 11/1997 | Hamersly | |
| 5,704,945 A | 1/1998 | Wagner et al. | |
| 5,706,822 A | 1/1998 | Khavari | |
| 5,711,746 A | 1/1998 | Carlson | |
| 5,720,713 A | 2/1998 | Hutchison | |
| 5,743,865 A | 4/1998 | Townsend | |
| 5,746,774 A | 5/1998 | Kramer et al. | |
| 5,755,645 A | 5/1998 | Miller et al. | |
| 5,857,989 A | 1/1999 | Smith, III | |
| 5,888,212 A | 3/1999 | Petrofsky et al. | |
| 5,890,996 A | 4/1999 | Frame et al. | |
| 5,893,891 A | 4/1999 | Zahedi | |
| 5,921,946 A | 7/1999 | Tillinghast et al. | |
| 5,961,085 A | 10/1999 | Navarro et al. | |
| 6,001,075 A | 12/1999 | Clemens et al. | |
| 6,022,301 A | 2/2000 | Fahlman | |
| 6,050,924 A | 4/2000 | Shea | |
| 6,050,963 A | 4/2000 | Johnson et al. | |
| 6,058,534 A | 5/2000 | Navarro et al. | |
| 6,066,110 A | 5/2000 | Nauert | |
| 6,074,355 A | 6/2000 | Bartlett | |
| 6,080,123 A | 6/2000 | Pansiera | |
| 6,113,642 A | 9/2000 | Petrofsky et al. | |
| 6,117,093 A | 9/2000 | Carlson | |
| D433,756 S | 11/2000 | Castillo | |
| 6,190,341 B1 | 2/2001 | Brim | |
| 6,263,531 B1 | 7/2001 | Navarro et al. | |
| 6,309,368 B1 | 10/2001 | Herzberg et al. | |
| 6,358,190 B1 | 3/2002 | Pellis | |
| 6,383,156 B1 | 5/2002 | Enzerink et al. | |
| 6,408,464 B1 | 6/2002 | Weismiller et al. | |
| 6,409,691 B1 | 6/2002 | Dakin et al. | |
| 6,409,693 B1 * | 6/2002 | Brannigan | 602/16 |
| 6,409,695 B1 | 6/2002 | Connelly | |
| 6,413,232 B1 | 7/2002 | Townsend et al. | |
| 6,423,098 B1 | 7/2002 | Biedermann | |
| 6,425,166 B1 | 7/2002 | Seligman et al. | |
| 6,436,018 B2 | 8/2002 | Pellis | |
| 6,436,058 B1 | 8/2002 | Krahner et al. | |
| 6,443,993 B1 | 9/2002 | Koniuk | |
| 6,447,424 B1 | 9/2002 | Ashby et al. | |
| 6,461,318 B2 | 10/2002 | Freeman et al. | |
| 6,464,657 B1 | 10/2002 | Castillo | |
| 6,470,520 B1 | 10/2002 | Weismiller et al. | |
| 6,500,139 B1 | 12/2002 | Townsend et al. | |
| 6,527,733 B1 | 3/2003 | Ceriani et al. | |
| 6,530,868 B1 | 3/2003 | Pape | |
| 6,537,237 B1 | 3/2003 | Hopkins et al. | |
| 6,540,708 B1 | 4/2003 | Manspeizer | |
| 6,540,711 B2 | 4/2003 | Cox | |
| 6,565,523 B1 | 5/2003 | Gabourie | |
| 6,592,538 B1 | 7/2003 | Hotchkiss et al. | |
| 6,610,023 B2 | 8/2003 | Steponovich | |
| 6,610,101 B2 | 8/2003 | Herr et al. | |
| 6,613,097 B1 | 9/2003 | Cooper | |
| 6,654,974 B2 | 12/2003 | Ruehl et al. | |
| 6,673,117 B1 | 1/2004 | Soss et al. | |
| 6,679,920 B2 | 1/2004 | Biedermann et al. | |
| 6,689,080 B2 | 2/2004 | Castillo | |
| 6,712,781 B1 | 3/2004 | Sheppard | |
| 6,719,806 B1 | 4/2004 | Zahedi et al. | |
| 6,726,644 B1 | 4/2004 | Pasij | |
| 6,740,054 B2 | 5/2004 | Stearns | |
| 6,746,414 B1 | 6/2004 | Devreese | |
| 6,749,537 B1 | 6/2004 | Hickman | |
| 6,752,774 B2 | 6/2004 | Townsend et al. | |
| 6,757,924 B2 | 7/2004 | Goodwin et al. | |
| 6,764,244 B2 | 7/2004 | Pansiera | |
| 6,764,520 B2 | 7/2004 | Deffenbaugh et al. | |
| 6,773,411 B1 | 8/2004 | Alvarez | |
| 6,793,641 B2 | 9/2004 | Freeman et al. | |
| 6,796,951 B2 | 9/2004 | Freeman et al. | |
| 6,796,952 B2 | 9/2004 | Nelson et al. | |
| 6,834,752 B2 * | 12/2004 | Irby et al. | 192/81 C |
| 6,854,145 B2 | 2/2005 | Ruehl et al. | |
| 6,857,153 B2 | 2/2005 | Ruehl et al. | |
| 6,875,187 B2 | 4/2005 | Castillo | |
| 6,878,126 B2 | 4/2005 | Nelson et al. | |
| 6,890,314 B2 | 5/2005 | Seligman | |
| 6,902,585 B2 | 6/2005 | Hikichi | |
| 6,911,050 B2 | 6/2005 | Molino et al. | |

| | | |
|---|---|---|
| 6,911,051 B2 | 6/2005 | Cheng |
| 6,913,586 B2 | 7/2005 | Engsberg et al. |
| 6,936,020 B2 | 8/2005 | Davis |
| 6,953,108 B2 * | 10/2005 | Anderfaas et al. ......... 188/267.2 |
| 6,953,442 B2 | 10/2005 | Yamasaki et al. |
| 6,960,177 B2 | 11/2005 | Turrini et al. |
| 6,962,571 B2 | 11/2005 | Castillo |
| 6,969,363 B2 | 11/2005 | Houser |
| 6,969,364 B2 | 11/2005 | Sterling |
| 6,971,996 B2 | 12/2005 | Houser |
| 6,981,957 B2 | 1/2006 | Knecht et al. |
| 6,994,682 B2 | 2/2006 | Bauerfeind et al. |
| 7,004,919 B2 | 2/2006 | Gaylord et al. |
| D517,248 S | 3/2006 | Castillo et al. |
| 7,011,641 B1 | 3/2006 | DeToro et al. |
| 7,037,287 B2 | 5/2006 | Cormier et al. |
| 7,044,925 B2 | 5/2006 | Castillo et al. |
| 7,044,926 B2 | 5/2006 | Carlson |
| 7,048,704 B2 | 5/2006 | Sieller et al. |
| 7,311,687 B2 * | 12/2007 | Hoffmeier et al. ............ 602/26 |
| 2002/0077575 A1 | 6/2002 | Cox |
| 2002/0143279 A1 * | 10/2002 | Porier et al. .................. 602/16 |
| 2002/0143297 A1 | 10/2002 | Porier et al. |
| 2003/0204156 A1 | 10/2003 | Nelson et al. |
| 2004/0002674 A1 | 1/2004 | Sterling |
| 2004/0054310 A1 | 3/2004 | Dadfarmay |
| 2004/0068215 A1 | 4/2004 | Adelson et al. |
| 2004/0167452 A1 | 8/2004 | Mason et al. |
| 2004/0176715 A1 | 9/2004 | Nelson |
| 2004/0204667 A2 | 10/2004 | Nelson et al. |
| 2004/0225245 A1 | 11/2004 | Nelson |
| 2004/0267177 A1 | 12/2004 | Houser |
| 2005/0102031 A1 | 5/2005 | Leonard |
| 2005/0148915 A1 * | 7/2005 | Nathanson et al. ............ 602/16 |
| 2005/0148916 A1 | 7/2005 | Nathanson |
| 2005/0192523 A1 | 9/2005 | Knecht et al. |
| 2005/0203455 A1 | 9/2005 | Cropper |
| 2005/0240134 A1 | 10/2005 | Brown |
| 2006/0089580 A1 | 4/2006 | Turrini et al. |
| 2006/0089581 A1 | 4/2006 | Lambert |
| 2006/0100560 A1 | 5/2006 | Gilmour |
| 2006/0100562 A1 | 5/2006 | Pamplin |

FOREIGN PATENT DOCUMENTS

| | | |
|---|---|---|
| EP | 0 382 976 B1 | 9/1993 |
| EP | 0 454 186 B1 | 11/1995 |
| WO | WO 01/45600 A1 | 6/2001 |
| WO | WO 01/49222 A1 | 7/2001 |
| WO | WO 01/49235 A2 | 7/2001 |
| WO | WO 02/02035 A1 | 1/2002 |
| WO | WO 02/02036 A1 | 1/2002 |
| WO | WO 02/02037 A1 | 1/2002 |
| WO | WO 02/02038 A1 | 1/2002 |
| WO | WO 02/26169 A2 | 4/2002 |
| WO | WO 02/34156 A2 | 5/2002 |
| WO | WO 02/085258 A2 | 10/2002 |
| WO | WO 03/004107 A1 | 1/2003 |
| WO | WO 03/103545 A1 | 12/2003 |
| WO | WO 2004/024040 A2 | 3/2004 |
| WO | WO 2004/069108 A2 | 8/2004 |
| WO | WO 2004/103483 A1 | 12/2004 |
| WO | WO 2005/018487 A2 | 3/2005 |
| WO | WO 2005/032437 A1 | 4/2005 |
| WO | WO 2005/067827 A2 | 7/2005 |
| WO | WO 2005/067828 A2 | 7/2005 |
| WO | WO 2005/099638 A1 | 10/2005 |
| WO | WO 2005/107659 A2 | 11/2005 |
| WO | WO 2006/012084 A1 | 2/2006 |
| WO | WO 2006/052761 A1 | 5/2006 |

* cited by examiner

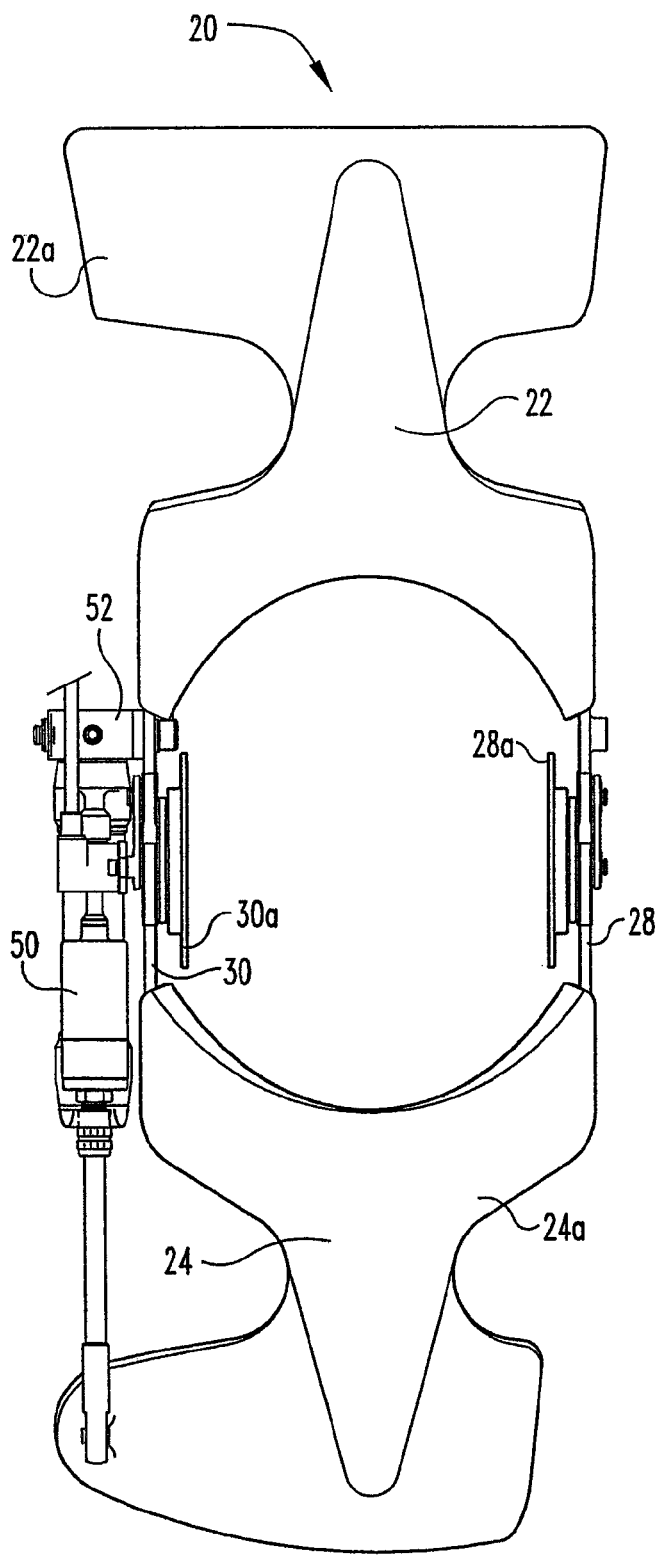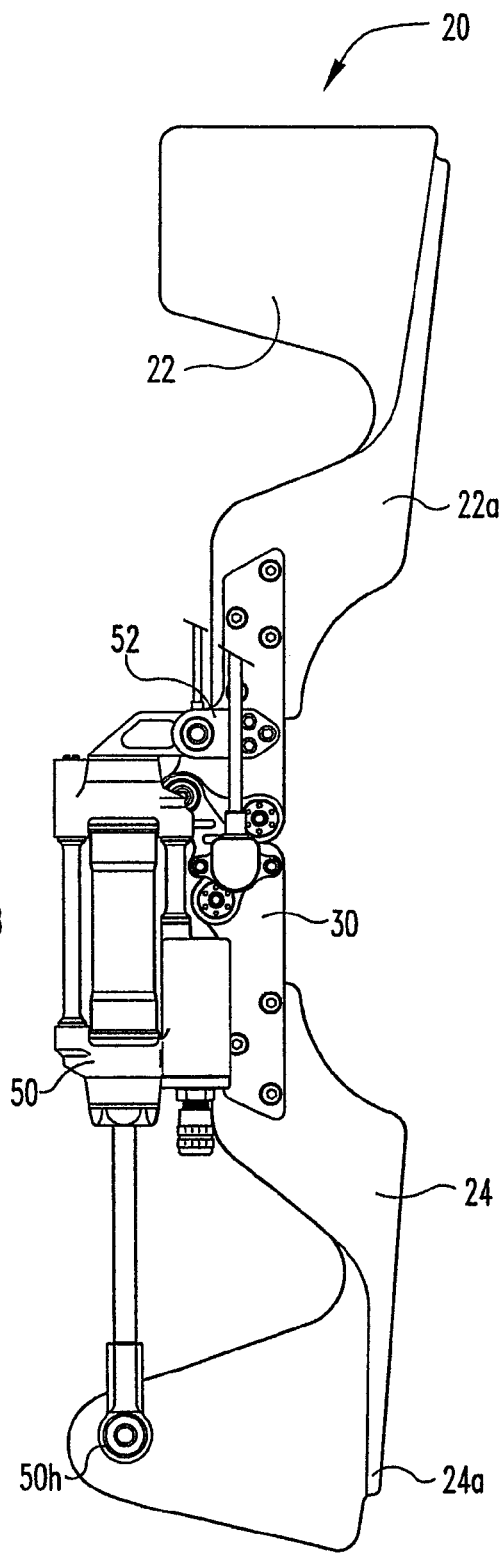
Fig. 1A Fig. 1B

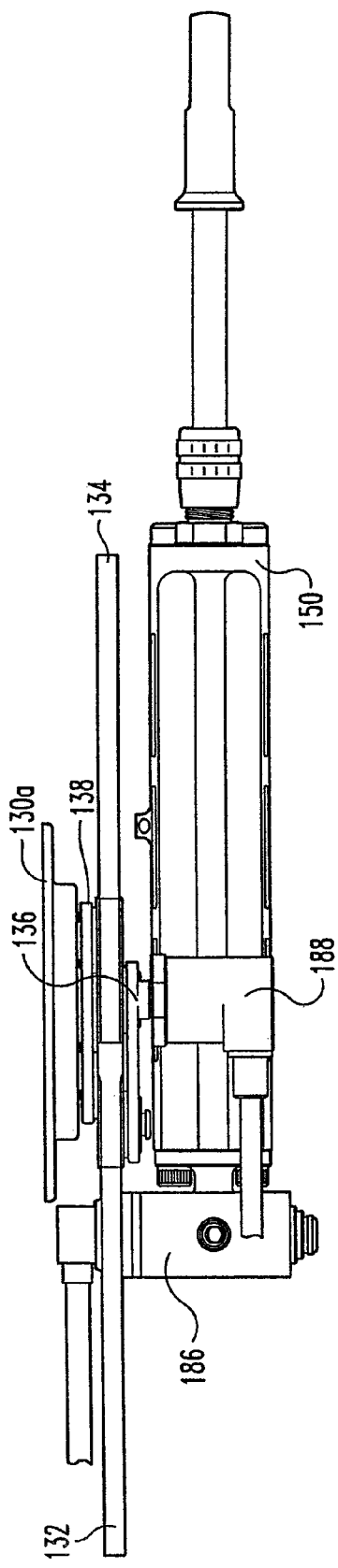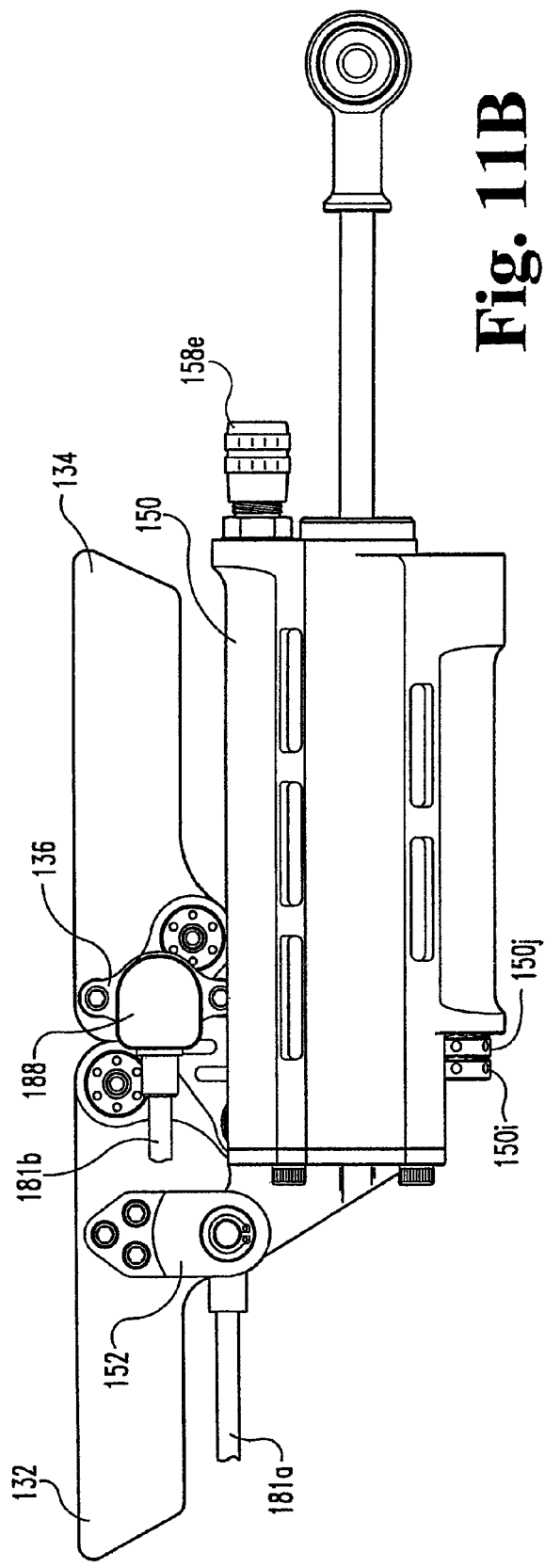

ORTHOTIC BRACE

CROSS REFERENCE TO RELATED APPLICATIONS

This application claims priority to U.S. Provisional Patent Application Ser. No. 60/697,426, filed Jul. 8, 2005; U.S. Provisional Patent Application Ser. No. 60/697,513, filed Jul. 8, 2005; and U.S. Provisional Patent Application Ser. No. 60/698,157, filed Jul. 11, 2005, all of which are incorporated herein by reference.

FIELD OF THE INVENTION

Various embodiments of the present invention pertain to methods and apparatus for supporting or replacing a joint of an animal, and in particular, for providing support for a human knee or for replacing a human knee.

BACKGROUND OF THE INVENTION

The knee joint is a uni-axial hinge joint. The knee moves in a flexion (bending of the knee) and extension (straightening of the knee) direction. The three major bones that form the knee joint are: the femur (thigh bone), the tibia (shin bone), and the patella (kneecap). The prime muscle movers of the knee joint are the quadriceps muscles (on top of the femur), which move the knee into extension; and the hamstring muscles (underneath the femur), which move the knee into flexion. The quadriceps muscles are made up of five muscles known as the rectus femoris, vastus lateralis, vastus medialis, vastus intermedius and a secondary muscle, the vastus medialis oblique (VMO). The hamstring is made up of three muscles known as the biceps femoris, semimembranosus, and semitendinosus. The hamstring to quadriceps muscle strength ratio is two-thirds; meaning, the hamstring should be approximately thirty-three percent weaker than the quadriceps. The muscles, ligaments, nervous system, and skeletal system work in unison to stabilize the knee during gait activities (walking, running, jumping).

The stability and integrity of the knee joint and supportive musculature are greatly affected by the nervous system (sensation-reaction) and edema (swelling). Even minimal amounts of pain and swelling are enough to alter the normal quadriceps-hamstring relationship, which decreases the knee joint's capability and integrity. When this relationship is compromised, one of three general scenarios is likely to result:

1. The person will be unable to perform at his or her previous physical level. Decreased performance levels will be evident and the possibility of tendonitis, sprains, and strains is increased.
2. The VMO/Quadriceps group will not operate at a level sufficient enough to prevent sudden buckling (collapsing) of the knee, risking injury to internal and external knee components.
3. The hamstring muscle group will not work at an efficient level to prevent hyperextension of the knee, risking injury through tearing internal knee components.

Common internal knee injuries include cartilage tears, meniscal tears, and ligamentous (ACL and PCL) tears. Common external knee injuries include muscular tears (hamstring, quadriceps, and gastro-nemius) and ligamentous tears (MCL and LCL). Most of the described injuries will cause loss of time from work and may require physical therapy and/or surgical intervention.

The Anterior Cruciate Ligament (ACL) is one of the most commonly injured knee ligaments with 250,000 injuries occurring each year, at a cost of approximately $100,000,000.00. For the patients who decide to undergo surgery and rehabilitation for an ACL injury, costs will exceed $4,000.00 in medical bills per injury. These costs do not include any durable medical equipment, which includes functional knee bracing, or lost time at work. Of these 250,000 injuries, seventy percent are non-contact injuries. There are three common ways to injure an ACL:

1. The most common occurrence of ACL injuries happens during deceleration of the body along with pivoting/cutting.
2. The ACL ruptures during knee hyperextension, as a result of decreased hamstring capabilities.
3. Movements and actions performed by the human body that are out of control, for which the knee is unable to adequately adjust, are common in combat.

The average recovery time for an athlete from an ACL injury varies from six months to more than a year. In order to combat this, many football linemen are currently wearing knee-bracing systems as a preventative tool. However, females have been shown to have a greater chance of injury than their male counterparts by two to eight times. With the military looking at expanding the role of females in combat and non-combat situations, the potential rise in lost time of service may increase in the future. The post-surgical ACL patient will require a functional brace after injury.

Current commercially available knee bracing apparatuses on the market for ligament and cartilage injuries are passive support systems. They work by minimizing excessive motions in certain planes to help prevent possible injury. Though many braces attempt to minimize the potential of a hyperextension injury, these braces do not minimize the chance of a buckling injury. Commercially available passive knee braces do not adequately address the issues of trying to control swelling and pain during gait activities.

Various embodiments of the present invention pertain to knee braces which provide novel and non-obvious apparatus and methods for support of human knees, and also for replacement of human knees.

SUMMARY OF THE INVENTION

Some embodiments of the present invention relate to apparatus and methods for supporting or replacing a joint between two limbs of an animal, such as a hip, knee, ankle, shoulder, or elbow joint.

Various embodiments of the present invention include a brace for a joint between two limbs of an animal, comprising a first attachment member for coupling to a first limb, and a second attachment member for coupling to a second limb. Yet other embodiments include a four bar linkage for interconnecting the first member relative to the motion of the second member. Still other embodiments include a damper for resisting the pivotal motion of the first member relative to the motion of the second member.

Some embodiments include a joint corresponding to a human joint, comprising a first member, and a second member. Still other embodiments include a first link rotationally connected to the first member and rotationally connected to the second member, the first link having a first length between rotational centers. Some embodiments include a second link rotationally connected to the first member and rotationally connected to the second member, the second link having a second length between rotational centers. In some embodiments, the first length is greater than or about equal to the second length. In other embodiments the first link and second link are not parallel.

Another embodiment of the present invention includes a joint corresponding to a human knee joint, comprising a femoral member and a tibial member. Some embodiments further include a first link having two ends and pivotally connected at a first end to said femoral member and pivotally connected at the second end to said tibial member; a second link having two ends and pivotally connected at a third end to said femoral member and pivotally connected at the fourth end to said tibial member. The first end is spaced apart from the third end by a first distance, the second end is spaced apart from the fourth end by a second distance, and the first distance is greater than the second distance.

Yet other embodiments include a joint corresponding to a human knee joint, comprising a femoral member and a tibial member. Other embodiments further include a first link having two ends and pivotally connected at a first end to the femoral member and pivotally connected at the second end to the tibial member. Still other embodiments include a second link having two ends and pivotally connected at a third end to said femoral member and pivotally connected at the fourth end to said tibial member. In some embodiments the first end, said second end, and said fourth end are generally aligned when the joint is at a position corresponding to full extension of a human knee joint.

Another embodiment of the present invention includes a method for supporting movement of a human knee. Some embodiments further include providing an upper leg support, a lower leg support, and a damper. Still further embodiments include pivotally interconnecting the upper leg support to the lower leg support by a four bar linkage. Other embodiments include resisting the pivotal movement of the upper leg support relative to the lower leg support with the damper.

Some embodiments of the present invention include a method for rehabilitating an animal joint, which includes sensing movement of one of the limb attachment members with a sensor, storing a history of the sensed movement, and modifying the resistive force characteristics of the resistive force device by the controller and in response to the history.

Yet other embodiments include a method for protecting an animal joint, which includes sensing flexing of a first limb toward the second limb by a sensor, calculating with a controller a value corresponding to the rate of flexing, comparing the value to a predetermined flexure rate limit, and changing the characteristics of a damper based on the comparison.

Yet other embodiments include a joint for replacing a knee joint of an animal, comprising, a femoral attachment member for coupling to an upper leg, a tibial replacement member for replacing a removed lower leg, and a four bar linkage interconnecting said femoral attachment member and said tibial replacement member, said linkage including a first link rigidly attached to said femoral attachment member, a second link rigidly attached to said tibial replacement member, a third link pivotally interconnecting said first link and said second link, and a fourth link pivotally interconnecting said first link and said second link.

Other aspects of various embodiments of the present invention will be apparent from the claims, text, and drawings to follow.

DESCRIPTION OF THE DRAWINGS

FIG. 1A is a frontal plan view of a knee brace according to one embodiment of the present invention.

FIG. 1B is a scaled side elevational view of the apparatus of FIG. 1A.

FIG. 11A is a side elevational view of a portion of the apparatus of FIG. 10.

FIG. 11B is a top plan view of the apparatus of FIG. 11A.

DESCRIPTION OF THE PREFERRED EMBODIMENT

Figure 2A:
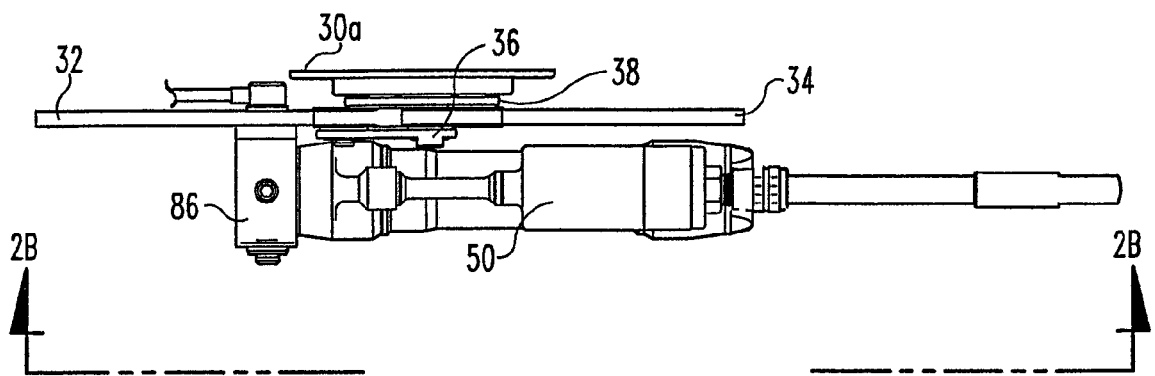
FIG. 2A is a side elevational view of a portion of the apparatus of FIG. 1A.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It is further understood that there is no single element, feature, aspect, concern, or advantage that is a requirement for every embodiment of the present invention, or for any embodiment of the present. Every use of the term "invention" herein refers to a specific embodiment, but not to all embodiments. Some of the drawings may be described as being drawn to scale. The use of scaled drawings is to show an example, and is not limiting on any embodiment of the present invention.

Some embodiments of the present invention pertain to an orthotic joint support assembly for a human knee. However, the present inventions are not so limited, and other embodiments pertain to joint support assemblies for the limbs of an animal.

One embodiment of the present invention pertains to an orthotic knee device which has multiple military applications (and commercial applications), as they relate to the current political and economical environment in which we are engaged. In some embodiments, the knee brace can perform multiple functions. First, as a conventional therapeutic device, the knee brace can be used to assist recovery from a pre-existing injury. Second, as a prophylactic device, the brace may be used to help prevent or reduce injury during arduous activity (i.e. training and combat), when excessive loads are applied to the knee joint. Also, as an active assisted device, the brace may be used to supplement normal muscular capability, when normal human physiological strength and reaction times will not be adequate to protect the soldier from sustaining an injury.

Some embodiments of the present invention reduce the work that is normally done by the quadriceps and hamstring muscles, without imposing undue restrictions on the movement of the leg. One embodiment incorporates a hydraulically driven shock system, which reduces the loads being placed on the external and internal knee joint structures. The shock system also provides a means of dissipating some of the energy that would normally be dealt with by the knee's musculature. This dissipation of energy will decrease the fatigue level of the knee, allowing for soldiers to perform at a higher level for a longer period of time. By reducing the loads on the knee joint and its associated muscular components, the chance of swelling and pain caused by most activity and motion is decreased, therefore resulting in reduction in pain and swelling results in the knee joint performing more consistently and with decreased chance of failure (i.e. injury).

In one embodiment, there is a knee support assembly with an upper leg attachment and a lower leg attachment. The two attachments are coupled together by interior and exterior joint assemblies. In one preferred embodiment, these joint assemblies comprise four-bar linkages. However, the present invention is not so limited, and other embodiments link the upper and lower leg attachments by simple, uniaxial pivots or by bicentric pivots. Additionally, other embodiments of the joint support assembly include abutting features that limit the movement of the upper attachment relative to the lower attachment in flexion, extension, or both flexion and extension.

A joint support assembly according to some embodiments of the present invention provides an alternative load path from the lower leg to the upper leg. Loads are normally transmitted from the lower leg through the knee joint to the upper leg. A knee support assembly with a force modifying apparatus provides an alternate path for loads to be transmitted between muscles of the lower leg and muscles of the upper leg, with these loads bypassing the knee joint. In some embodiments, the force modifying apparatus is adjusted to provide more damping force (and therefore increased load bypassing of the knee joint) during flexion of the knee, such as when a person squats, as when a person goes down a stairway, or as when a person riding in a vehicle such as a boat has the floor of that vehicle suddenly rise toward the person.

In some embodiments, the force modifying apparatus has a second adjustment which can provide a smaller damping force during extension of the knee joint. By having a force modifying apparatus that provides less resistance to extension than to flexion, it is easier for a person to walk and more freely extend their leg (when the knee joint is generally unloaded), yet have the knee support apparatus provide a bypass path for loads during flexion (when the knee may be supporting some or all of the person's weight).

Although what has been described is a force modifying apparatus with higher resistance to flexion than extension, the present invention is not so constrained. In other embodiments, the extension forces can be greater than the flexion forces. Such embodiments may be useful for exercising a knee joint, especially when the person is seated in a chair.

In addition to altering the load path from the lower leg to the upper leg, those embodiments of the present invention incorporating a damper also provide a means for dissipating the load being bypassed as the addition of heat to the damping fluid. The combination of lower loads on the knee and dissipation of some of the loads provides a general decrease in the fatigue level of the knee, allowing the user to perform at a higher level for a longer period of time.

Some embodiments of the present invention also include a force modifying apparatus that interconnects the upper and lower leg attachments. This force modifying apparatus can be a damper mechanism which provides a force which opposes flexion of the joint, extension of the joint, or both flexion and extension. In some embodiments this opposing force is a function of the angular velocity of the upper leg attachment relative to the lower leg attachment. In yet other embodiments the opposing force is also, or alternatively, a function of the angular displacement of the upper leg attachment relative to the lower leg attachment. In still other embodiments the opposing force is also, or alternatively, a function of the history of the angular velocity and/or the angular position of the upper leg attachment relative to the lower leg attachment.

In some embodiments the force modifying apparatus is a fluid damper, such as a hydraulic or pneumatic damper. In one embodiment, the force modifying apparatus is a hydraulic shock absorber whose resistance is a function of direction, velocity, and manual adjustment setting. In some embodiments the fluid damper is a linear device, such as with a piston and rod that extend out from a cylinder. In yet other embodiments the fluid damper is of the rotary type. An example of a rotary damper can be found in U.S. Pat. No. 7,048,098 to Moradian, and also in U.S. Patent Application Publication No. 2006/0096818 A1 (to Moradian).

In one embodiment of the present invention, a knee support assembly includes upper and lower leg attachments interconnected by interior and exterior joint assemblies. Each of the joint assemblies are adapted and configured to permit less than full flexion of a knee. In one embodiment, the knee support assembly includes impact-resistant covers for the front side of the upper leg and the front side of the lower leg, as well as a cover for the front of the knee. One application for this embodiment is as a leg protector for a catcher of a baseball team.

Yet other embodiments of the present invention include a joint support assembly which includes an electronic data logger. In some embodiments, this data logger records electrical signals which are related to the load being transmitted by the force modifying apparatus, the angular position of the upper leg attachment relative to the lower leg attachment, and/or the angular velocity of the upper leg attachment relative to the lower leg attachment.

Various dimensions and materials are described herein. It is understood that such information is by example only, and is not limiting to the inventions.

FIGS. 1A and 1B show scaled frontal and side views of a joint support assembly 20 for a human knee. Assembly 20 includes an upper leg attachment 22 and a lower leg attachment 24. Each of these attachments 22 and 24 include rigid bodies 22a and 24a, respectively, which are coupled to the upper leg (UL) and lower leg (LL) by one or more straps (not shown). The upper and lower attachments 22 and 24 are placed above and below, respectively, a person's knee. However, the present invention is not limited to support of human knees, and can be used with other joints, such as human elbow joints. Further, the devices and methods described herein are not limited to humans, but can also be applied to limbs of other animals.

Upper and lower attachments 22 and 24 are interconnected on one side by an interior joint assembly 28 and on the other side by an exterior joint assembly 30. In some embodiments, the interior and exterior joint assemblies 28 and 30 include inner pads 28a and 30a, respectively, which provide a smooth cushioned interface between the respective joint assemblies and the sides of the person's knee. In one embodiment, upper and lower rigid bodies 22a and 24a are fabricated from a synthetic material with integral reinforcements such as carbon fibers, aramid fibers or glass fibers.

FIGS. 1A and 1B depict a knee support assembly 20 for a right leg. It is understood that the present invention also pertains to left legs. In some embodiments, a knee support assembly for a left leg is a mirror image of the assembly 20 shown in FIGS. 1A and 1B. In applying the apparatus and methods described herein to human joints other than knees, and also to animal joints other than human joints, it is preferred that the force modifying apparatus 50 be located to the exterior of the animal's limb, although the present invention is not so limited and the force modifying apparatus can be on either side of the support assembly, or on both sides.

Figure 2B:
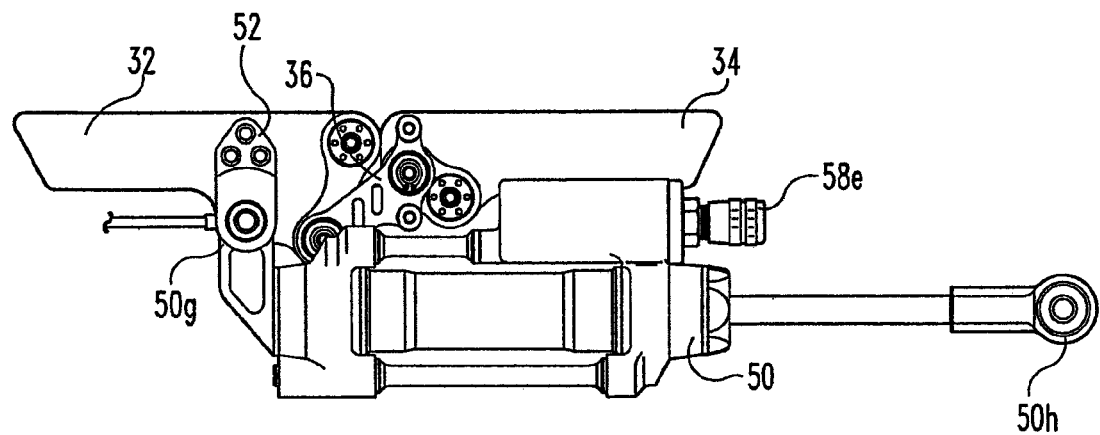
FIG. 2B is a view of the apparatus of FIG. 2A as taken along line 2B-2B of FIG. 2A.

FIGS. 2A and 2B show side and frontal views, respectively, of a portion of the apparatus of FIGS. 1A and 1B. FIGS. 2A and 2B show an exterior joint assembly 30 interconnected with a force modifying apparatus 50. Joint assembly 30 includes an upper link 32 interconnected to a lower link 34 by a first interconnecting link 36 and a second interconnecting link 38. As best seen in FIG. 1B, upper and lower links 32 and 34 are fastened to upper rigid body 22a and lower rigid body 24a, respectively. However, the present invention also contemplates those embodiments in which these links are attached to their respective rigid bodies by any method, including bonding by adhesives, fusion under heat, welding, and brazing, as examples. Further, the present invention contemplates those embodiments in which upper link 32 is integral with rigid body 22a and lower link 34 is integral with lower rigid body 24a. In one embodiment, links 32, 34, 36, and 38 are fabricated from materials such as titanium, aluminum, or steel. As one example, joint assemblies 28 and 30 are fabricated from titanium such as 6AL-4V.

Figure 22:
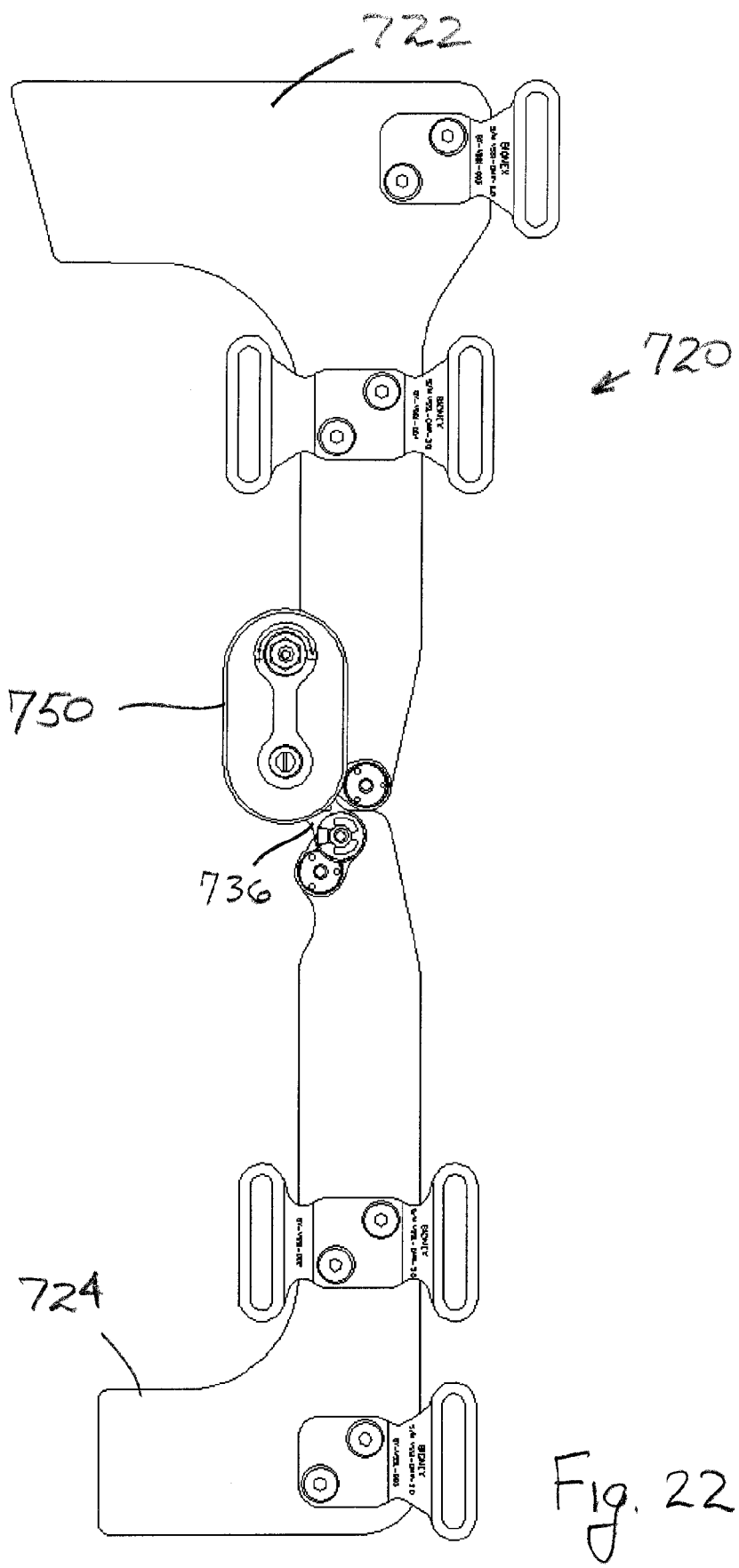
FIG. 22 is a side elevational view of an orthotic brace according to another embodiment of the present invention.

FIG. 22 is a side elevational view of a knee brace 720 according to another embodiment of the present invention. Knee brace 720 includes a rotary damper 750. Rotary damper 750 in one embodiment is of the vane type, although in other embodiments it has a toroidal flow path. The rotational input to the damper 750 is by way of interconnecting link 736. The housing of damper 750 is attached to the rigid portion of attachment 722. As the user's limb flexes, link 736, which is rigidly attached to a vane (not shown) within damper 750, pivots. The vane moves within a chamber, and displaces fluid through an orifice, thus creating a resistive moment on interconnecting link 736. It is understood that the present invention also contemplates those embodiments in which the housing (including the swept hydraulic chamber) of damper 750 is attached to the lower limb attachment 724, and the internal piston (vane type or cylindrical) is coupled to the pivot end of either of the interconnecting link of the four bar linkage.

Figure 3A:
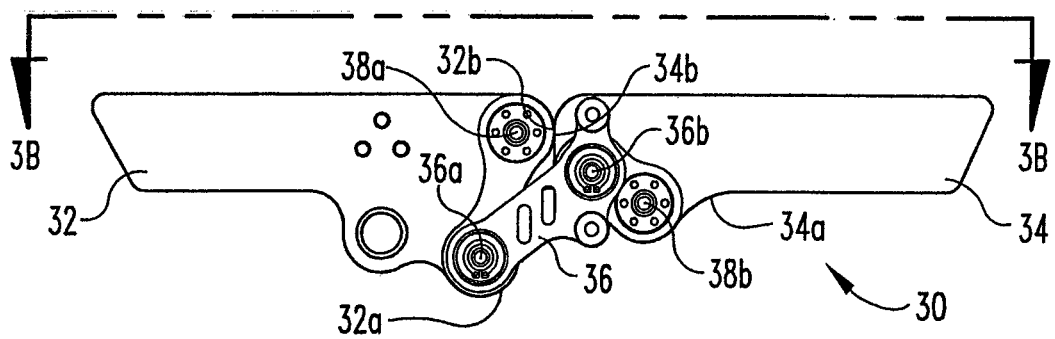
FIG. 3A is a scaled plan view of a portion of the apparatus of FIG. 1B.
Figure 3B:
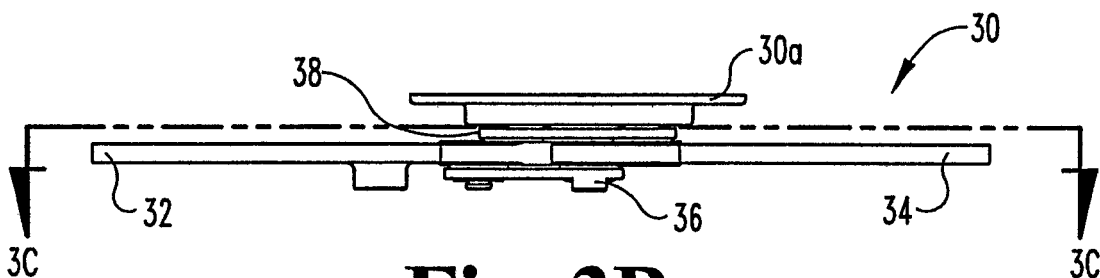
FIG. 3B is a view of the apparatus of FIG. 3A as taken along line 3B-3B of FIG. 3A.
Figure 3C:
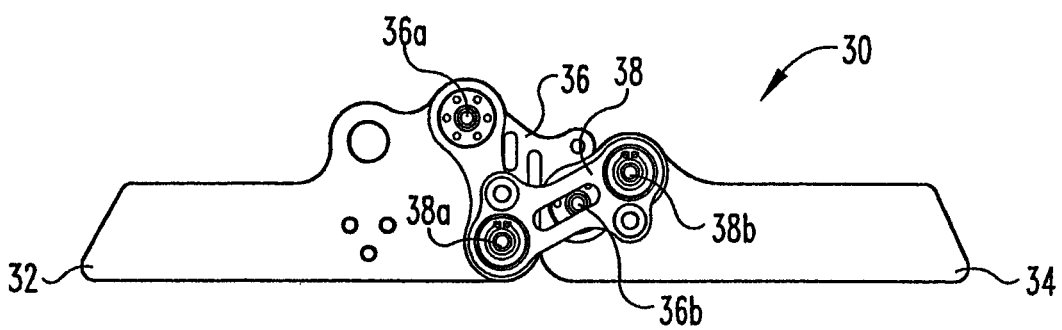
FIG. 3C is a view of the apparatus of FIG. 3B as taken along line 3C-3C of FIG. 3B.

FIGS. 3A, 3B, and 3C show various scaled views of a joint assembly 30 for the right leg of a human knee according to one embodiment of the present invention. The corresponding exterior joint assembly for the left leg of a human knee is a mirror image of assembly 30. Exterior joint assembly 30 includes an upper link 32 pivotally connected to a lower link 34 by first and second interconnecting links 36 and 38. As best seen in FIG. 3B, in one embodiment upper and lower links 32 and 34 are substantially coplanar. Interconnecting link 38 is located on the interior side of links 32 and 34 (i.e. closest to the knee joint). Inner pad 30a is a smooth, semi-rigid interface between the joint assembly and the joint, providing a degree of comfort to the user. Interconnecting link 36 is located to the exterior of links 32 and 34.

Figure 3D:
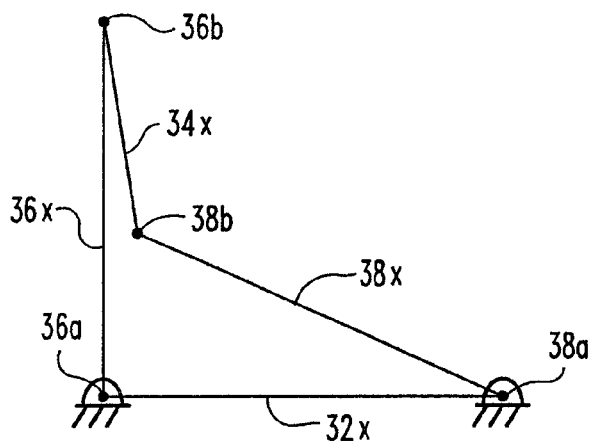
FIG. 3D is a schematic representation of the hinge apparatus of FIG. 3A with the hinges shown in the full flexion position.
Figure 3E:
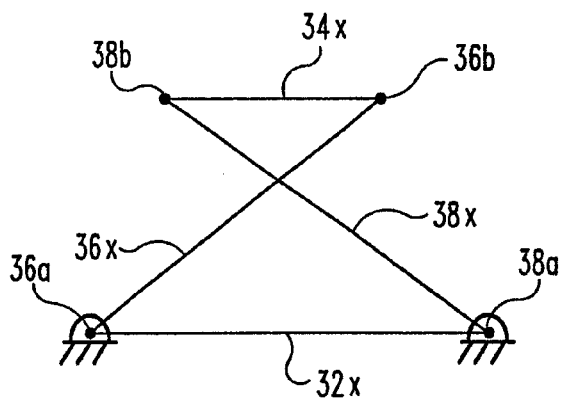
FIG. 3E is a schematic representation of the hinge apparatus of FIG. 3A with the hinges shown midway between the full flexion and full extension positions.
Figure 3F:
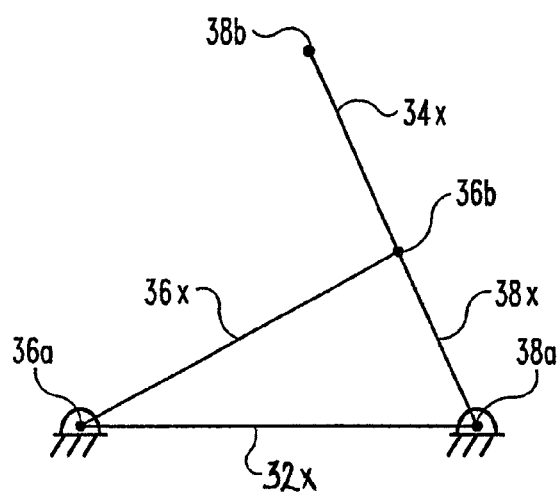
FIG. 3F is a schematic representation of the hinge apparatus of FIG. 3A with the hinges shown in the full extension position.

FIGS. 3D, 3E, and 3F are schematic representations of a four bar linkage which represents joint assembly 30. These figures as well as FIGS. 3A-3F depict the pivot centers for joint assembly 30. Interconnecting link 36 (a third link) is pivotally connected to upper link 32 (a first link) about pivot center 36a (a first pivot joint), and is pivotally connected to lower link 34 (a second link) about pivot center 36b (a second pivot joint). Interconnecting link 38 (a fourth link) is pivotally connected to upper link 32 (first link) about pivot center 38a (a third pivot joint) and is pivotally connected to lower link 34 (second link) about pivot center 38b (a fourth pivot joint).

Referring to FIGS. 3D, 3E, and 3F, the distance between pivot centers 36a and 38a is the distance 32x; the distance between pivot centers 36b and 38b is the length 34x. The length of interconnecting link 36 between its pivot centers 36a and 36b is represented by 36x. The length of interconnecting link 38 between its pivot centers 38a and 38b is represented by 38x.

Referring to FIGS. 3F and 3C, joint assembly 30 is shown in a position corresponding to full extension of the knee. In one embodiment of the present invention, joint assembly 30 includes a pair of rotational stops which limit movement of the knee beyond full extension. As shown in FIG. 3A, upper and lower links 32 and 34 are adapted and configured to have abutting features 32b and 34b, respectively, which contact each other at full extension. Abutting features 32b and 34b are flat, radiused surfaces of their respective upper and lower links which are designed for repeated contact with each other. In some embodiments, the surfaces are adapted and configured to include hardened surfaces to minimize wear. These hardened surfaces can result from attachment of separate, hardened pieces to the upper and lower links, chemical treatment of the contacting surfaces, and/or heat treatment.

FIG. 3D is a schematic representation of joint assembly 30 corresponding to full flexion of the knee. Referring to FIG. 3A, during full flexion of the knee there is abutting contact between features 32a and 34a of links 32 and 34, respectively. Surfaces 32a and 34a preferably have complementary shapes, with surface 32a being convex and surface 34a being concave. The use of complementary shapes for the abutting features provides lower bearing stresses during contact, thus decreasing wear and/or allowing increased load-carrying. In some embodiments, abutting features 32a and 34a are adapted and configured to come into abutment before the knee achieves full flexion. In such embodiments, an attempt by the user to fully flex the knee will result in contact prior to full flexion. In those cases where the person is squatting, this early abutment (prior to full flexion) results in an increased share of the load of the knee joint being transmitted instead through the upper and lower links to their respective upper and lower leg attachments and to the upper and lower leg muscles.

The present invention also contemplates those embodiments in which the extension rotational stops 32b and 34b have complementary shapes, and also including those embodiments in which the abutting surfaces are substantially flat and straight. Further, the present invention contemplates those embodiments in which the flexion rotational stops 32a and 34a are not complementary, and also those embodiments in which the abutting surfaces are substantially flat and straight. Further, the present invention contemplates those embodiments in which the flexion rotational stops 32a and 34a have been hardened as described above for the extension rotational stops.

Further, the present invention also contemplates those embodiments in which at least one of the abutting features 32b and 34b, and in which one of the abutting features 32a and 34a are adjustable. For example, the upper link or lower link can be adapted and configured to include a rotational member such as a fastener which can be moved relative to the link to which it is threadably attached, and further locked in place. Also, the present invention contemplates those embodiments in which at least one of the links 32 or 34 are adapted and configured to include an easily separable separate member which can be selected from a family of separate members of differing thicknesses. A particular member of a specific thickness could be fastened to the upper or lower link (such as by a rivet), and then replaced with a different member of the family having a different thickness after the first member has worn, or if the knee brace is being used by a person having a different flexion or extension limit.

As previously discussed, FIG. 3D corresponds to a joint assembly in full flexion and FIG. 3F corresponds to a joint assembly in full extension. FIG. 3E corresponds to a joint assembly midway between full extension and full flexion. As best seen in FIG. 3E, interconnecting links 38 and 36 (as represented by the distance between pivot centers 38x and 36x, respectively) form a criss-cross pattern when joint assembly 30 is in a midway position. During full flexion, distance 34x is substantially aligned with the length 36x. During full extension, distance 34x is substantially aligned with distance 38x. Referring to FIGS. 3D and 3E, it can be seen that in moving the knee joint from full flexion toward extension that the angle 38b-38a-36a decreases until pivot centers 36b, 38b and 38a are collinear. After that, the angle 38b-38a-36a increases until it achieves the angular relationships shown in FIG. 3F.

In one embodiment, the distance between pivot centers 38a and 38b is about 1.08 inches; the distance between pivot centers 38b and 36b is about 0.45 inches; the distance between pivot centers 36b and 36a is about 1.03 inches; and the distance between pivot centers 36a and 38a is about 0.93. Non-dimensionally, the distance between pivot centers 38a and 38b is about 1; the distance between pivot centers 38b and 36b is about 0.42; the distance between pivot centers 36b and 36a is about 0.95; and the distance between pivot centers 36a and 38a is about 0.86. The present invention contemplates dimensions and non-dimensional ratios other than those provided. As one example, the present invention contemplates a range of non-dimensional ratios; the distance between pivot centers 38a and 38b is about 1±0.1; the distance between pivot centers 38b and 36b is about 0.42±0.4; the distance between pivot centers 36b and 36a is about 0.95±0.1; and the distance between pivot centers 36a and 38a is about 0.86±0.9. It is understood that these dimensions, ratios, and ranges are by example only, and are not limiting to any of the embodiments of this invention.

Figure 4:
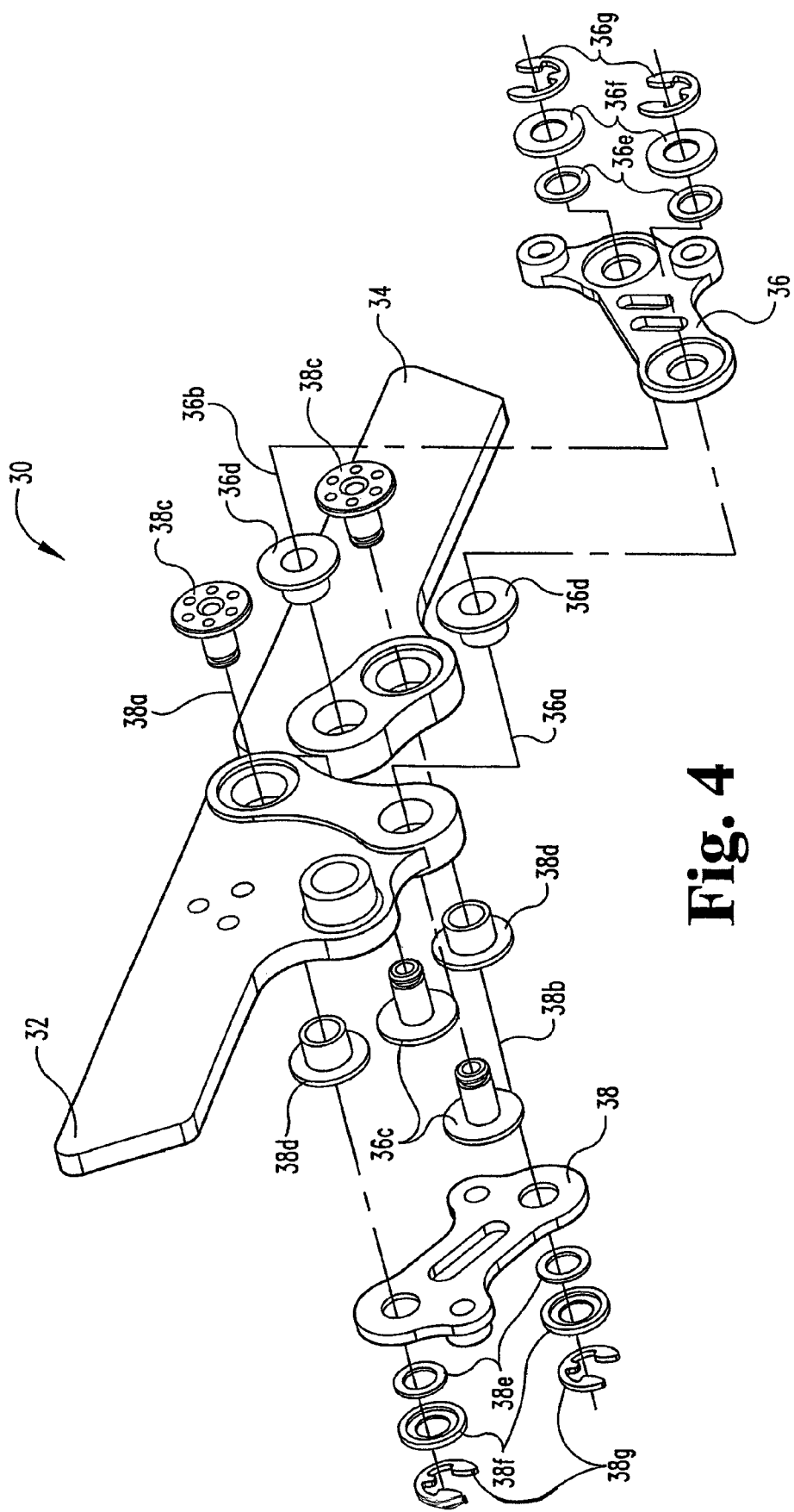
FIG. 4 is an exploded perspective view of the apparatus of FIG. 3A.

FIG. 4 shows an exploded perspective view of joint assembly 30. Each pivot joint of the linkage is comprised of similar components. For sake of brevity, the pivot joints of exterior interconnecting link 36 will be described. The same description applies to components 38c, d, e, f, and g.

FIG. 4 shows a plurality of components that establish pivot joint centerline 36a. These components include a coupling 36c which includes a flat head and a shank. The shank includes a groove for attachment of fastener. The shank of coupling 36c is received within the interior diameter of a plain bearing 36d. Bearing 36d includes a substantially flat head and a shank which receives the shank of coupling 36c on the interior, the exterior surface of the shank being in pivotal contact with the inner diameter of a hole of upper link 32. The shank of coupling 36c further extends through a hole in inner connecting link 36. A flat washer 36e and stepped washer 36f are also received over the shank of coupling 36c. An e-clip 36g is received within the groove of the shank and maintains the aforementioned assembly of components. In one embodiment, bearing 36d is a plain bearing fabricated from a low friction synthetic material. However, other embodiments of the present invention include the use of roller bearings and/or ball bearings.

Figure 5A:
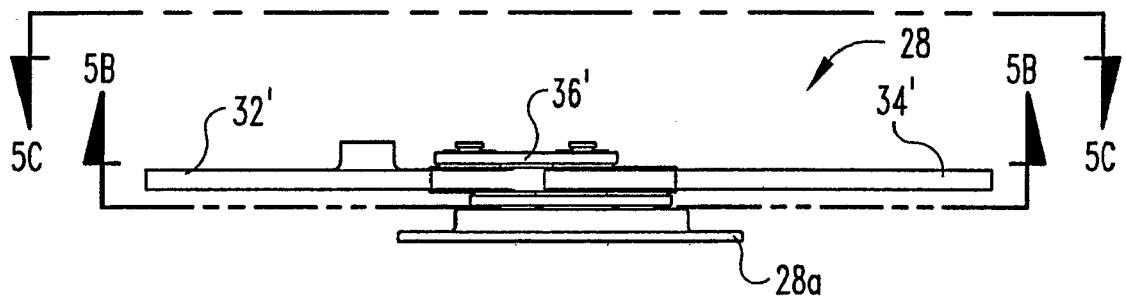
FIG. 5A is a side elevational view of a hinge apparatus according to one embodiment of the present invention.
Figure 5B:
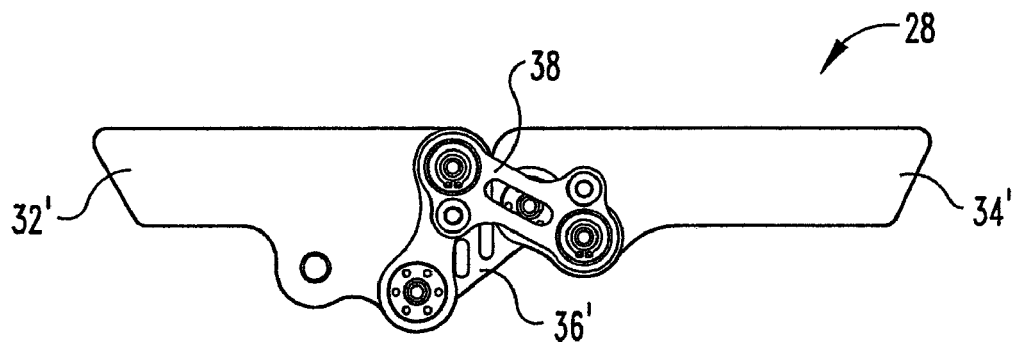
FIG. 5B is a view of the apparatus of FIG. 4A as taken along line 5B-5B of FIG. 5A.
Figure 5C:
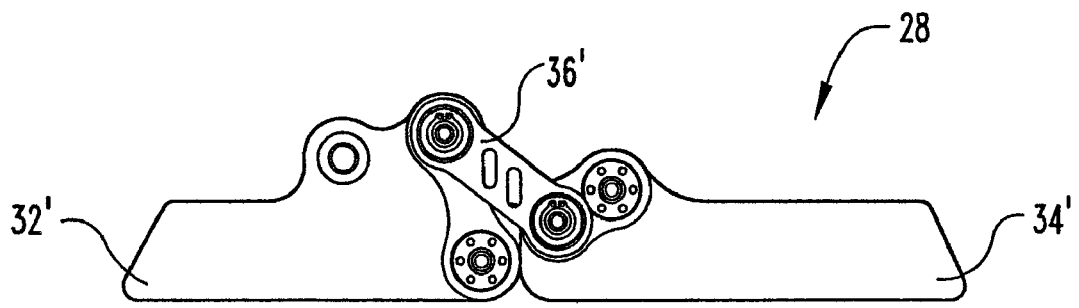
FIG. 5C is a view of the apparatus of FIG. 4A as taken along line 5C-5C of FIG. 5A.

FIGS. 5A, 5B, and 5C show various scaled views of interior joint assembly 28. The use of a prime (') designation after an element number (XX') denotes an element that is substantially the same as the non-prime element (XX), except for those changes shown and described.

Interior joint 28 includes a pair of upper and lower links 32' and 34', respectively, that are interconnected by first and second interconnecting links 36' and 38'. Interior joint assembly 28 is partly a mirror image of exterior joint assembly 30. Some embodiments of the present invention previously shown and described include a force modifying apparatus interconnected to the exterior joint assembly, without a corresponding force modifying apparatus interconnected to the interior joint assembly. However, the present invention also contemplates those embodiments in which a force modifying apparatus is interconnected to the interior joint assembly 28. This interior force modifying apparatus can be substantially the same as apparatus 50, but also includes those embodiments having interior force modifying apparatuses which are small and simpler. The present invention also contemplates those embodiments in which there is a force modifying apparatus interconnected to the interior joint but not a second apparatus interconnected to the exterior joint.

Figure 6:
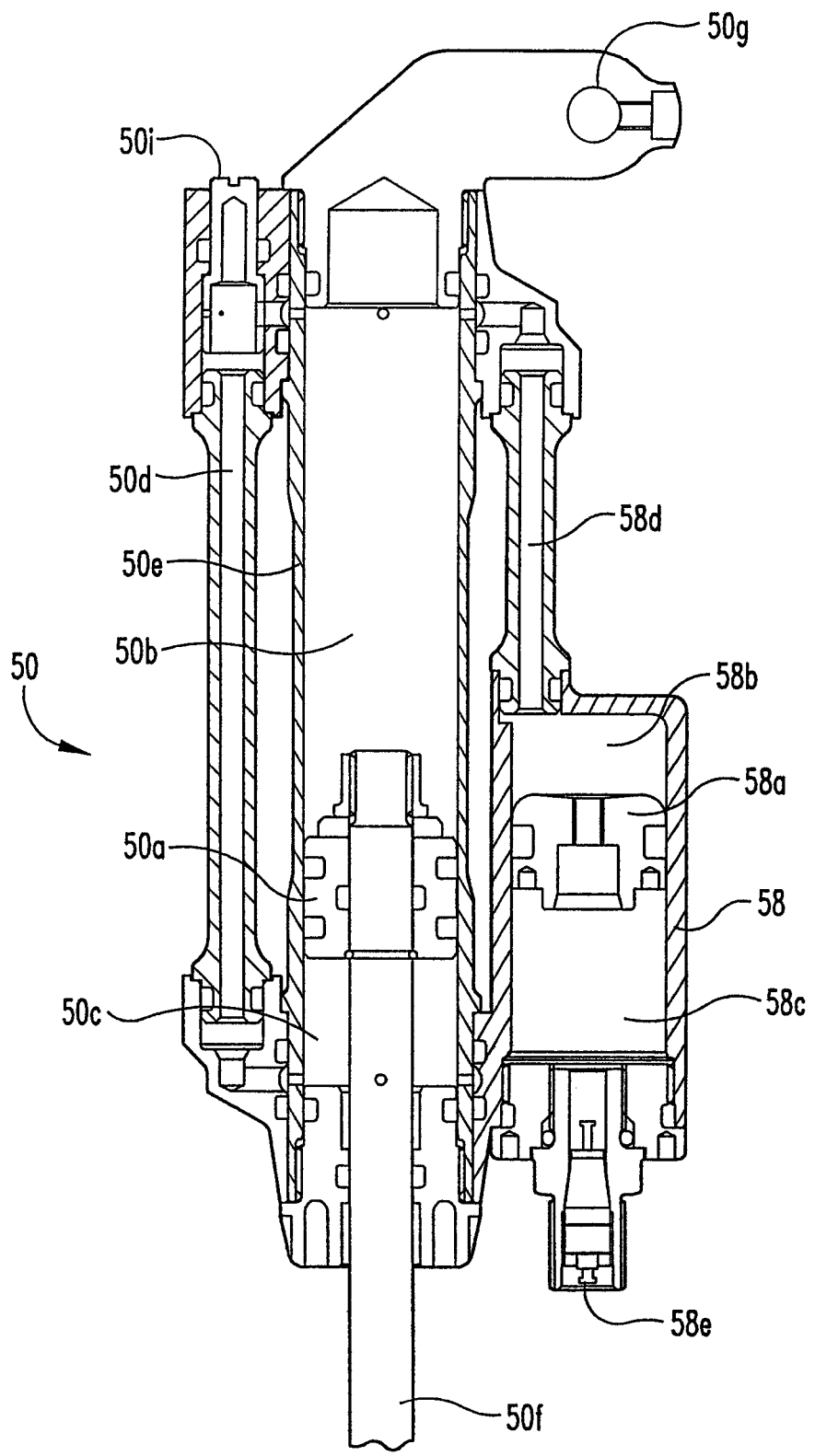
FIG. 6 is a cross-sectional view of a force modifying apparatus according to one embodiment of the present invention.

FIG. 6 is a cutaway of a force modifying apparatus 50 according to one embodiment of the present invention. In one embodiment, apparatus 50 provides a damping force related to a relative velocity, similar to a shock absorber for a vehicle suspension. Apparatus 50 includes a piston 50a which divides a cylinder into first and second chambers 50b and 50c. Piston 50a is attached to a shaft 50f, the end of shaft 50f including a Heim type rod-end bearing 50h which is pivotally connected to lower leg rigid body 24a (see FIGS. 1A and 1B). Piston 50a is received within a cylinder defined by body 50e. One end 50g of body 50e is pivotally connected to upper leg rigid body 22a (see FIGS. 1A and 1B).

Referring again to FIG. 6, as piston 50a and shaft 50f stroke upward and reduce the capacity of chamber 50b, hydraulic fluid is displaced laterally in two directions. Some hydraulic fluid passes through an orifice and fluid interconnection 58d into a chamber 58b of an accumulator 58. Also, fluid can go through an orifice on the opposite side of body 50e into an adjustable restriction 50i and through another fluid interconnection 50d.

Fluid passing through interconnection 58d into chamber 58b results in downward displacement of accumulator piston 58a into chamber 58c. In some embodiments of the present invention, accumulator 58 includes a pressure fitting 58e through which a gas such as nitrogen can be introduced into chamber 58c. This gas acts as a pneumatic spring during stroking of piston 50a within body 50e. Further, the gas-filled chamber 58c provides for changes in the volume of the hydraulic fluid as it changes temperature.

Fluid being displaced from chamber 50b can also flow through the adjustable restriction 50i. Restriction 50i includes an end which is slotted, hex shaped, knurled, or otherwise adapted and configured for external adjustment either by a tool or by hand. Fluid passing through adjustable restriction 50i and into fluid interconnection 50d is returned to enlarging chamber 50c through an orifice. This combination of adjustable orifice and accumulator provides variation in the applied damping force that is related to both displacement and velocity.

Figure 7A:
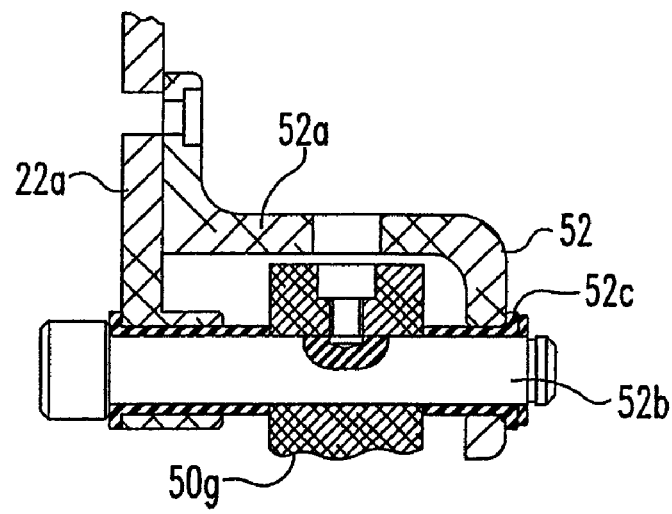
FIG. 7A is a cross-sectional view of a connection to the apparatus of FIG. 6.
Figure 7B:
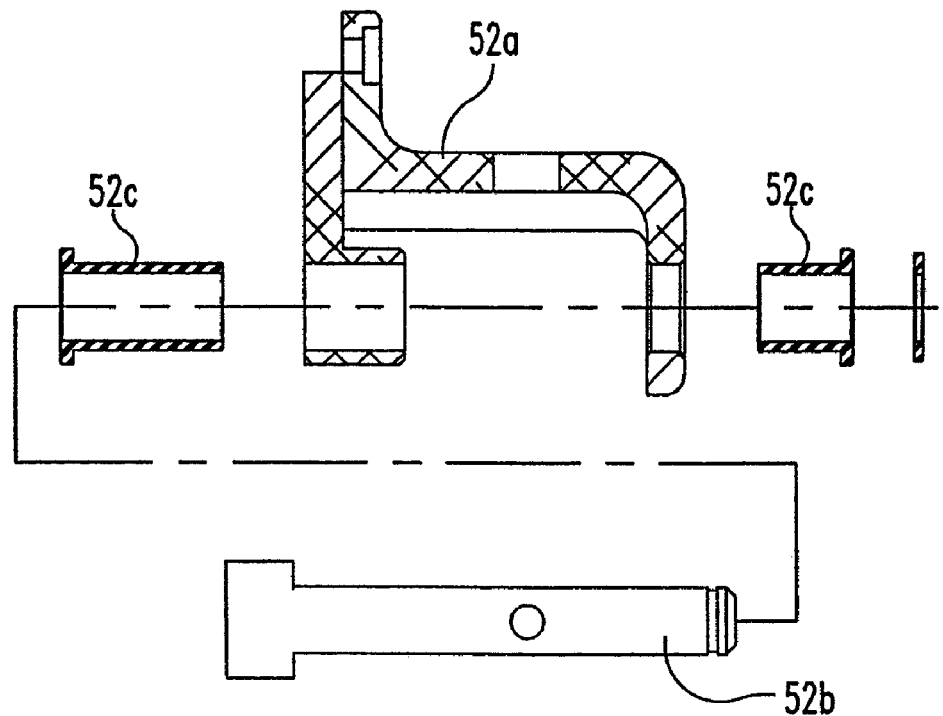
FIG. 7B is an exploded view of the apparatus of FIG. 7A.

FIGS. 7A and 7B show cross sectional and exploded views, respectively, of the attachment of end 50g of force modifying apparatus 50 to rigid body 22a of upper leg attachment 22. The attachment of the force modifying apparatus to the rigid body is preferably by secure, stable mounts in order to minimize localized deflections of the rigid body. The end 50g is supported on a shaft 52b (which can also be a fastener). One end of shaft 52b is supported by a plain bearing 52c within the inner diameter of a hole in bracket 52a. The other end of shaft 52b is supported by a plain bearing within a hole of rigid body 22a. Bracket 52a is fastened to rigid body 22a by a three bolt pattern (best seen in FIG. 1B).

In some embodiments, end 50g includes a hole which can be lined up with an indentation within shaft 52, such that end 50g and shaft 52b can be connected together by a setscrew. A fastener such as an e-clip attaches together the joint assembly mounted on shaft 52b.

Figure 8B:
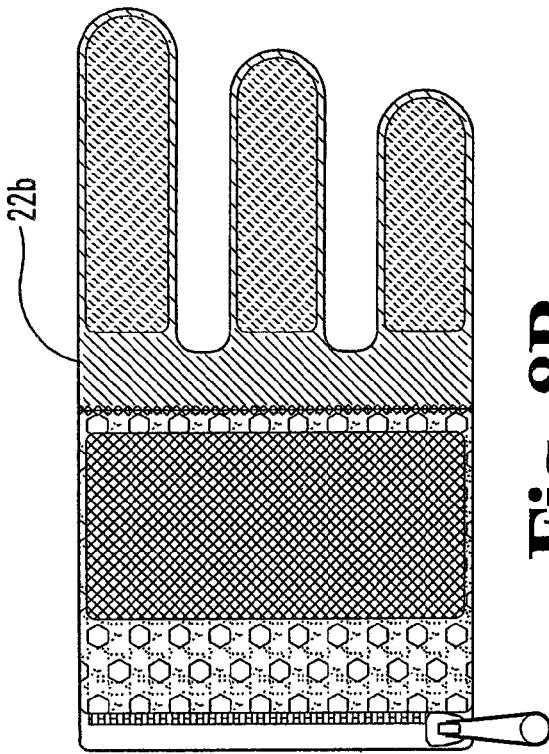
FIG. 8B is a top plan view of a strap according to one embodiment of the present invention.
Figure 8D:
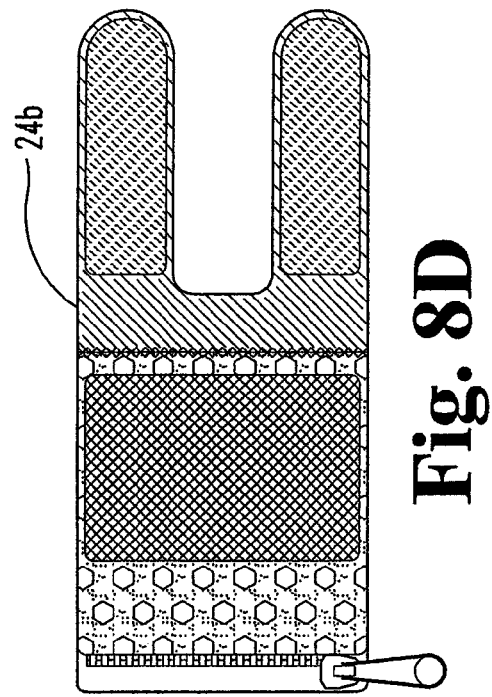
FIG. 8D is a top plan view of a strap according to one embodiment of the present invention.
Figure 8A:
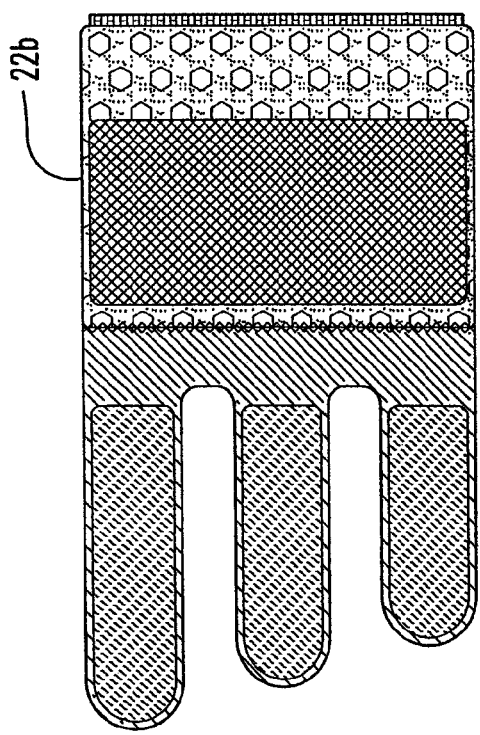
FIG. 8A is a top plan view of a strap according to one embodiment of the present invention.
Figure 8C:
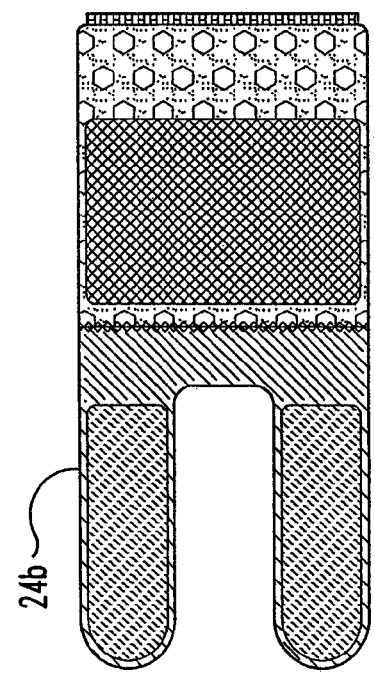
FIG. 8C is a top plan view of a strap according to one embodiment of the present invention.

FIGS. 8A, 8B, 8C, and 8D, show the straps which assist in attaching upper and lower rigid bodies 22a and 24a to the upper and lower leg, respectively. FIGS. 8A and 8B show halves of straps 22b which are interconnected in one embodiment by a zipper. The non-zippered end of the straps 22b include a plurality of flexible fingers which can be passed through loops (not shown) on rigid body 22a, and then self adhered to another part of the same strap by hook and loop-type fasteners. FIGS. 8C and 8D show halves of a lower strap assembly 24b which attaches rigid body 24a to the lower leg in a similar manner.

FIGS. 9-12 pertain to another embodiment of the present invention. The use of an N-prefix in front of an element number (NXX) refers to an element that is substantially the same as the non-prefixed element (XX), except as shown and described.

FIGS. 9-12 pertain to a knee support assembly 120 according to another embodiment of the present invention. Assembly 120 includes an upper leg attachment 122 and a lower leg attachment 124 as previously described, although including fitment bladders and pumping mechanisms. Upper leg attachment 122 includes a flexible bladder 122c which is interposed between rigid body 122a and the upper leg (UL), and also between the straps 122b and the upper leg. Lower leg attachment 124 likewise includes a bladder 124c disposed between the lower leg (LL) and the rigid body 124a and the straps 124b. In one embodiment, bladders 122c and 124c include corresponding push button pumps 122d and 124d, respectively. By use of these pumps, the person can selectively pump and pressurize (or by a release mechanism deflate) the corresponding bladder, and thereby adjust the degree of tightness of the respective leg attachment assembly to the leg itself. The bladders 122c and 124c can be filled with a gas, liquid, or gel. In one embodiment, rigid bodies 122a and 124a are constructed of carbon fiber composites with the respective links 132 and 134 molded into the corresponding rigid bodies. In one embodiment, the straps 122b and 124b are fabricated from neoprene and nylon. The straps include neoprene interliners which can be removed and cleaned or replaced.

Figure 9:
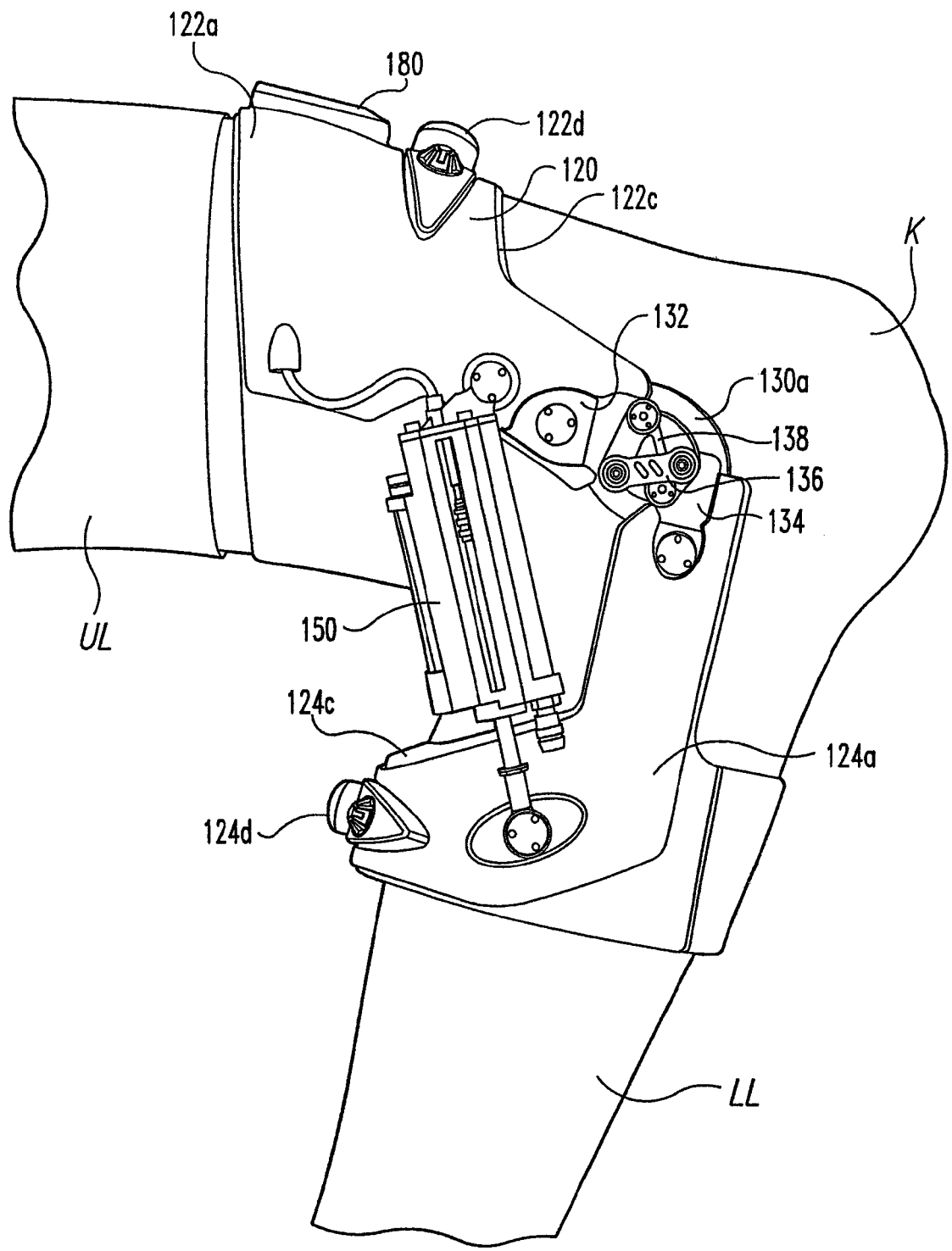
FIG. 9 is a side elevational view of a knee brace according to another embodiment of the present invention as shown on a flexed knee.
Figure 10:
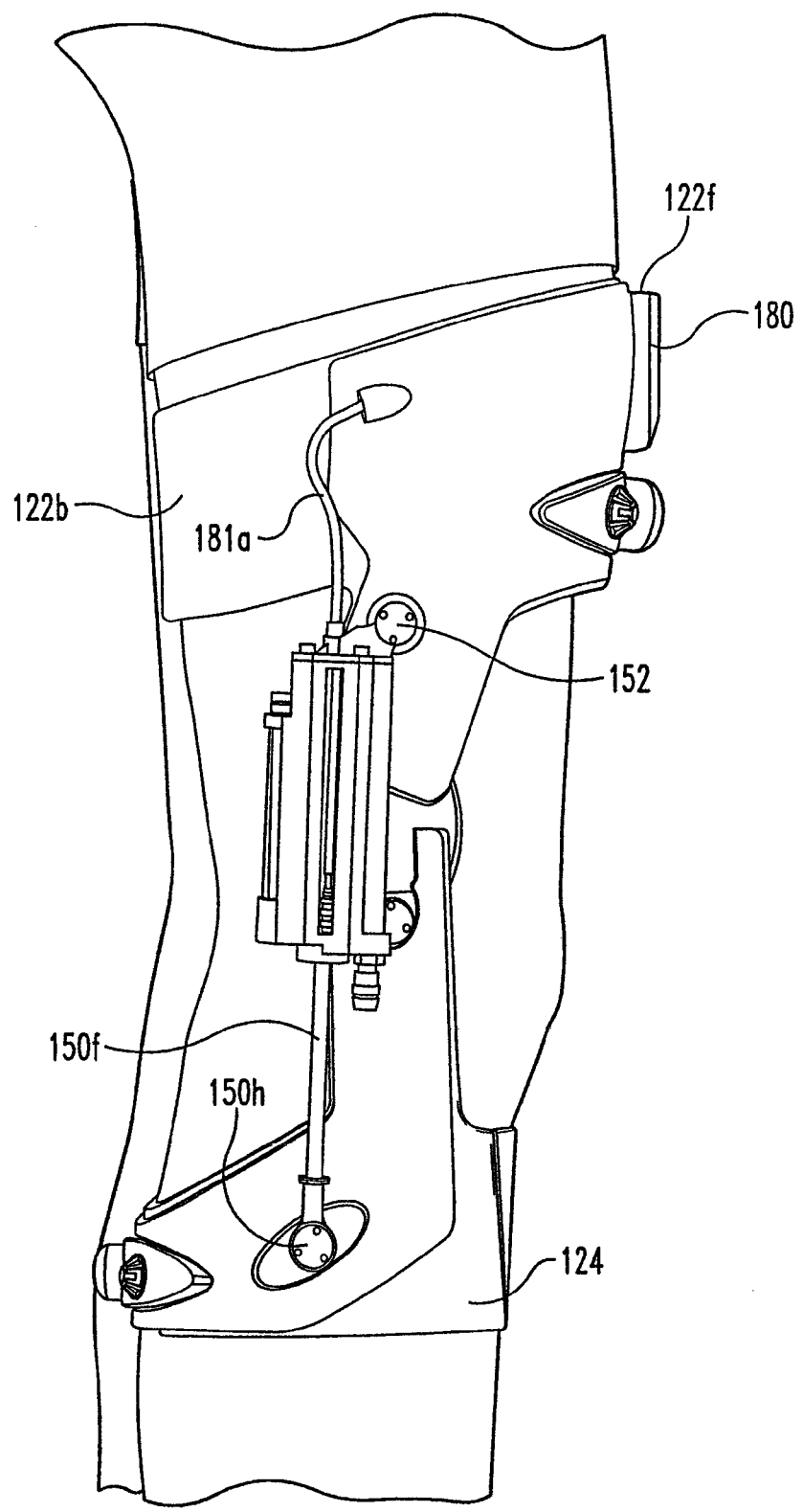
FIG. 10 shows the apparatus of FIG. 9 on an extended knee.

FIGS. 9 and 10 (both scaled drawings) also show side views of an electronic controller or computer 180 mounted to a pad 122f of the rigid body 122a. Software 1100 resident in some portions of memory 180b includes various algorithms for monitoring and recording various parameters measured from apparatus 120. In some embodiments, the resident software is operably connected to one or more actuators which can modify the operation of the knee brace apparatus. Further, computer 180 includes various communication interfaces for transmission and receipt of data and commands, including by hardwire (such as RS-232, RS-422, and MILSTD-1553 standards), fiber optic links, and wireless means (such as by infrared and radio wave signals). Computer 180 includes the circuitry and algorithms which establish the time of day. Computer 180 includes a processor 180a and various types of memory 180b (both not shown). Computer 180 is powered by a battery pack (not shown). Computer 180 is interconnected to various sensors by a plurality of interconnections 181 which are at least partly physically integrated into the rigid bodies 122a and 124a.

FIGS. 11A, 11B, 12A, and 12B show one embodiment of the present invention which includes various mechanical to electrical transducers. An angular position sensor 188 is mounted to a pair of mounting holes on interconnecting link 136. Sensor 188 provides an electrical signal to computer 180 through interconnection 181b that corresponds to rotational movement of link 136. This electrical signal can be manipulated by the software 100 to provide an output which corresponds to the relative position of the upper leg (UL) relative to the lower leg (LL). Further, this positional signal can be manipulated to provide data representing the relative angular velocity of upper leg (UL) relative to lower leg (LL). In one embodiment, position sensor 188 is a rotary potentiometer.

Figure 12A:
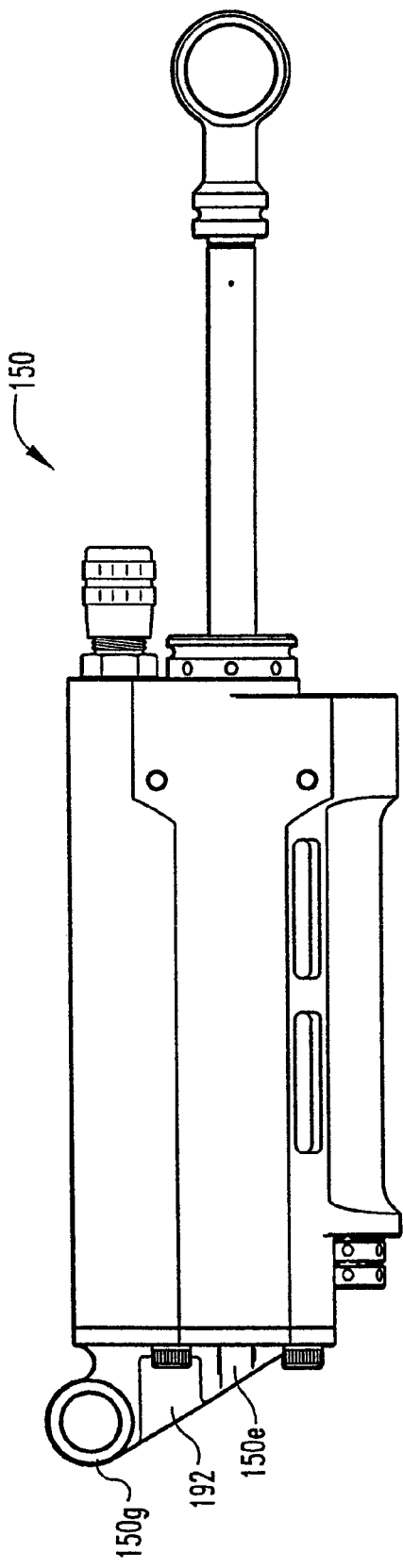
FIG. 12A is a top plan view of a force modifying apparatus according to another embodiment of the present invention.

In some embodiments, force modifying apparatus 150 includes one or more load transducers which produce signals corresponding to the magnitude of the damping force being applied between upper and lower rigid bodies 122*a* and 124*a*, respectively. Referring to FIG. 12A, a strain gage 192 is mounted to a thinned section of body 150*e* proximate to the body pivotal attachment 150*g*. A signal from strain gage 192 corresponding to surface strain of the thinned pocket of body 150*e* is transmitted by an electrical interconnection 181*a* to computer 180. This strain signal can be manipulated to data corresponding to the load being applied by force modifying apparatus 150.

Figure 12B:
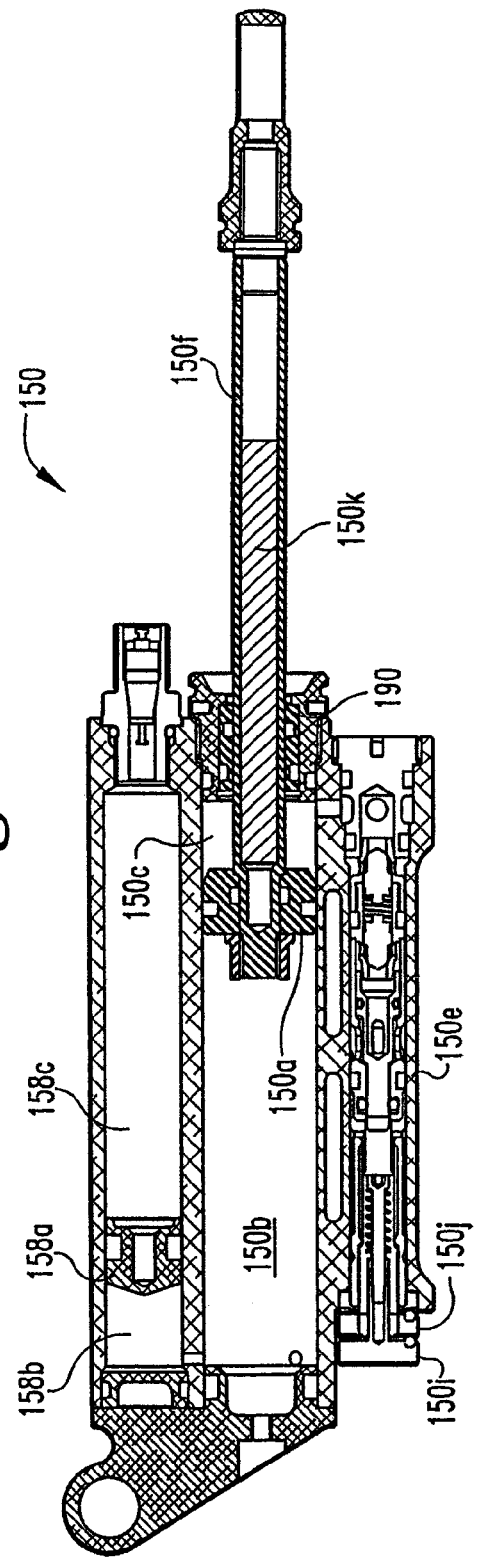
FIG. 12B is a cross-sectional view of the apparatus of FIG. 11A.

Referring to FIG. 12B, in one embodiment of the present invention shaft 150*f* is hollow and contains a magnetic core piece 150*k*. This magnetic core interacts with a Hall Effect sensor 190 mounted within the rod support of apparatus 150 to produce an electrical signal corresponding to the position of shaft 150*f* relative to body 150*e*. This signal is provided to computer 180 by interconnection 181*a*, and can be further manipulated into data which corresponds to the velocity of shaft 150*f* relative to body 150*e*. Yet other embodiments of the present invention include linear velocity transducers for measuring the velocity of the damper shaft.

Force modifying apparatus 150 has a smaller overall size than apparatus 50 in order to minimize protrusion of the apparatus for a person in a sitting or bending position. Still referring to FIG. 12B, a pair of adjustable fluid restrictions 150*i* and 150*j* are shown. Adjustable restriction 150*i* establishes an orifice size for flow of fluid from one of the chambers 150*b* or 150*c*, and therefore a damping force characteristic for movement of shaft 150*f* in a first direction. The second adjustable restriction 150*j* adjusts the orifice size for flow of fluid from the other of the chambers 150*b* or 150*c*, and therefore the damping force, for movement of shaft 150*f* in the opposite direction. In some embodiments, the force modifying apparatus is fabricated from 6AL-4V titanium, 7075-T6 aluminum, and polyamide plastics.

In some embodiments of the present invention the force modifying apparatus 150 utilizes a magnetorheological (MR) fluid, and also includes the electrical connections to apply a voltage to the MR fluid under the control of electronic controller 180. In such embodiments, the controller 180 can apply a voltage to modify the characteristics of the MR fluid in accordance with algorithms of the software 100. One example of a force modifying apparatus using an MR fluid is U.S. Pat. No. 6,279,702, issued Aug. 28, 2001 (to Koh), which incorporated herein by reference. In yet other embodiments, the force modifying apparatus includes an electrical actuator, the actuation of which modifies the resistive force characteristics of the apparatus. As one example, the resistive force characteristics can be modified by actuating a solenoid which changes the size of an orifice through which the hydraulic fluid passes.

In one embodiment of the present invention, software 100 includes an algorithm for rehabilitating a knee joint that has been damaged. In such situations, an orthopedic specialist may prescribe a regimen of joint movements to be undertaken while wearing support apparatus 120. As one example, the rehabilitation regimen can include a predetermined number of leg movement cycles (such as from extension to flexion) as a function of time. The patient could be asked to perform at least X number of cycles per time period, but not to exceed Y number of cycles in that time period, the quantities X and Y being functions of time. When the person completes the minimum X number of cycles, the information would be stored in memory for later retrieval by the orthopedic specialist or the person's insurer. However, if the person tries to exceed Y cycles, controller 180 will apply a voltage to the MR fluid sufficient to greatly increase the damping force and/or lock up the piston 150*a* within its cylinder. Additionally or alternatively, controller 180 could set off an audible alarm to warn the user that he is exceeding his prescribed regimen.

In yet another rehabilitative algorithm, the user is limited to movement of the knee support apparatus 120 over angular ranges that are functions of time. For example, soon after the injury or surgery, the algorithm permits limited angular movement of the upper leg relative to the lower leg, such as movement from full extension to no more than Z degrees of flexion, the quantity Z being a function of time. Immediately after the injury or surgery, the quantity Z maybe relatively small, but thereafter increasing over time until the user is ultimately allowed to fully flex the knee joint. If at any time the user attempts to bend the knee more than the allowed quantity Z, controller 180 applies a voltage to the MR fluid to greatly increase the damping force, or even to lock up piston 150*a* within its cylinder.

Further, it is understood that the aforementioned rehabilitative algorithms can be combined. Software 100 can include an algorithm which varies any or all of the quantities X, Y, and Z over time. Further, as discussed previously, controller 180 also monitors the movements of the user's knee for later downloading to a healthcare professional, such as a doctor or insurer. In addition, the algorithms for quantities X, Y, and Z could be programmed remotely by a healthcare professional for those embodiments which include wireless communication capability.

Figure 13:
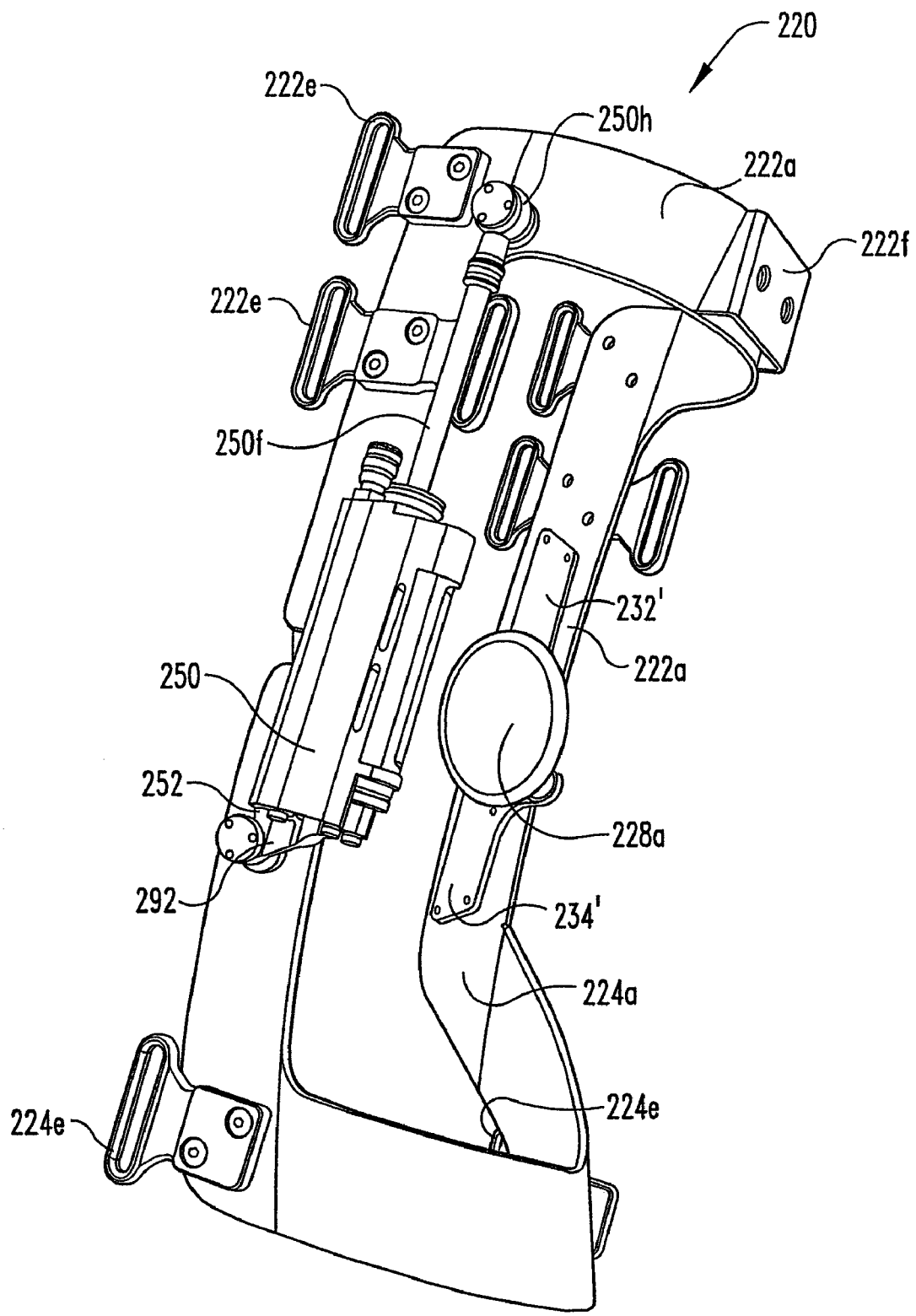
FIG. 13 is a perspective view of a knee brace according to another embodiment of the present invention.

FIG. 13 depicts a knee support assembly 220 according to another embodiment of the present invention. Force modifying apparatus 250 is oriented such that shaft 250*f* is pivotally connected by a Heim-type joint 250*h* to the upper rigid body 222*a*. Connector assembly 252 attaches the other end of force modifying apparatus 250 to the lower rigid body 224*a*.

Also shown in FIG. 13 is a plurality of loops 222*e* that are attached to upper rigid body 222*a*. A pair of loops 224*e* is attached to lower rigid body 224*a*. These loops are adapted and configured for interconnection with a strap 222*b* (upper) or 224*b* (lower) for fastening of knee support assembly 220 to a person. FIG. 12B also shows a mounting surface 222*f* for attachment and electrical interconnection of a computer 280.

Figure 14:
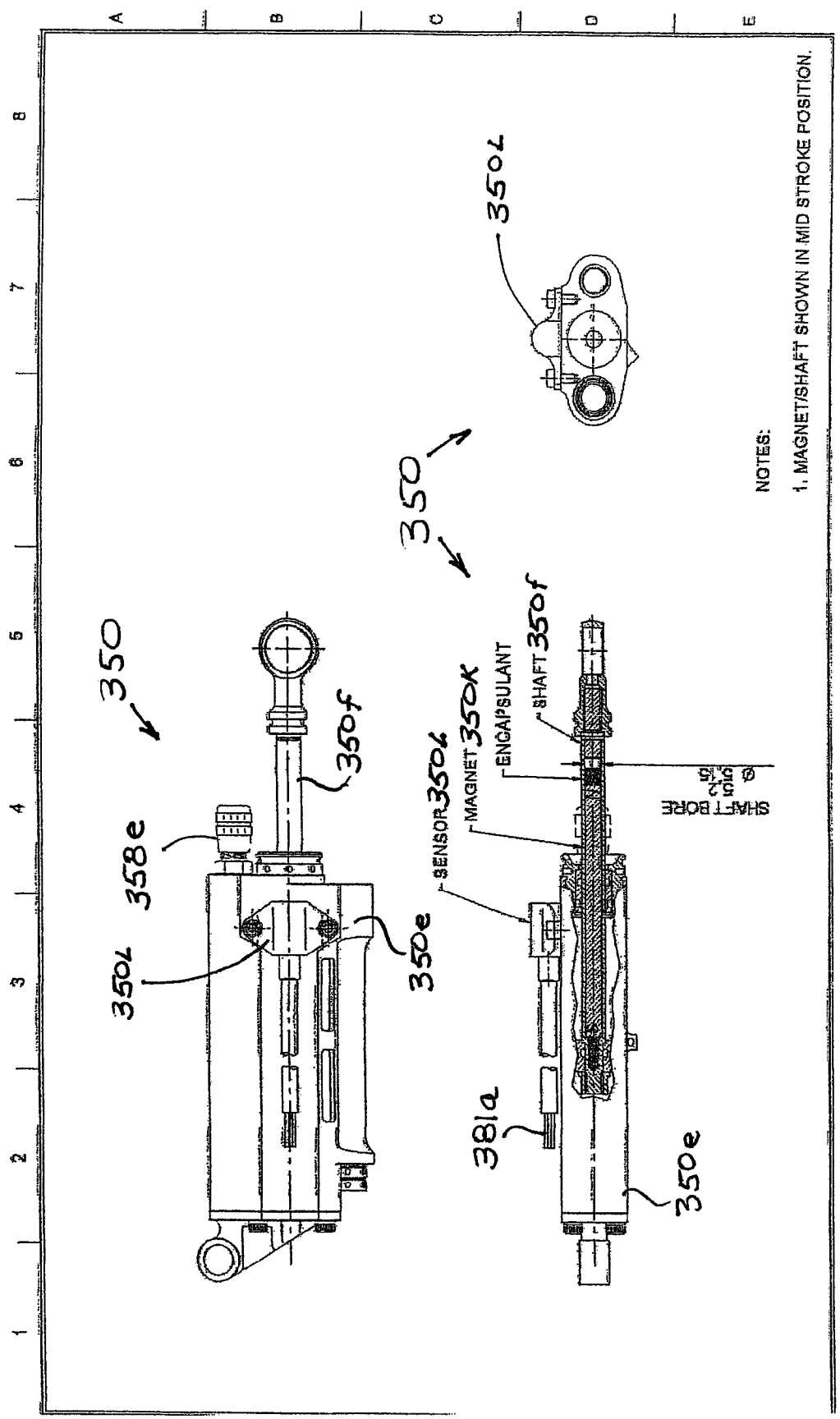
FIG. 14 shows top plan, side cross-sectional, and end views (all orthogonal) of a force modifying apparatus embodiment of the present invention.
Figure 15:
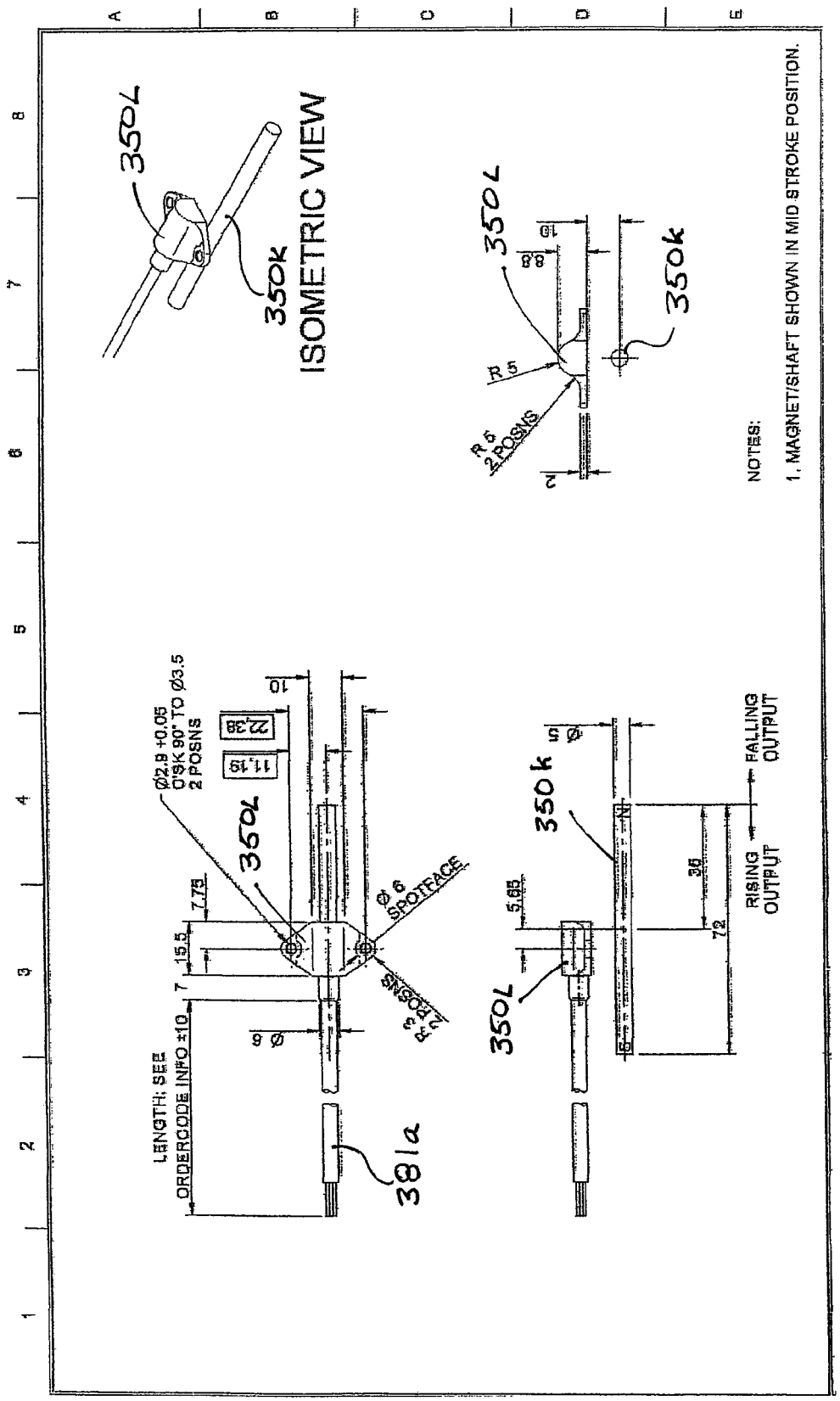
FIG. 15 shows various views of a portion of the apparatus of FIG. 15.

FIGS. 14-15 provide specifications and drawings of Hall-effect sensor for a force modifying apparatus according to one embodiment of the present invention. Apparatus 350 includes a magnet 350*k* within a shaft 350*f*. A transducer 350L is fastened to body 350*e*, and provides an electrical signal corresponding to the placement of shaft 350*f* relative to body 350*e*. FIGS. 14 and 15 include exemplary dimensions in millimeters.

In one embodiment, the output of a Hall Effect sensor is a voltage which changes in proportion to the shaft extension. A constant voltage is placed across the supply and ground wires of the sensor. The sensor consists of a Hall Effect element, and a shaft which houses a magnet. When the position of the sensor changes relative to the shaft, the change in magnetic field in the sensor results in a change in output voltage. Electrical characteristics of a Hall Effect sensor according to one embodiment of the present invention include the following: maximum applied voltage 15V; electrical stroke 70 mm; supply current <10 mA; output voltage @0 mm=0.2±0.05V (@25° C.; output voltage @70 mm=4.8±0.05V (@25° C.; non-linear output (output results supplied for 2 mm intervals over full electrical stroke); output voltage clamped between 0.1V and 4.9V; hysteresis due to magnet rotation 4% FS typ; insulation resistance >100 Mohm @500Vdc; and thermal shift <0.05% FS/K. Mechanical characteristics of a Hall Effect sensor according to one embodiment of the present invention include: weight less than 50 g; aluminum alloy body, hard anodized and dyed black; and titanium shaft (to be supplied by customer). In one embodiment of the present invention, Hall Effect sensor is designed to meet the following environment: resistant to standard motorsport fluids; maximum humidity 100%; operating temperature −40 to +125° C.; and vibration 50 to 2500 Hz @40 g 8 hrs per axis.

Yet other embodiments of the present invention include active and semi-active elements. In these embodiments, the use of active and semi-active elements, along with various sensors and a controller, permit the brace to become reactive to a situation. This reactive capability is the result of a dynamically adjustable shock and power-assistive devices incorporated into the brace. The power-assistive capabilities will allow for the brace to augment the normal muscular force during activities as well as when the muscle becomes fatigued. An electronic controller, upon sensing a failure in the integrity of the knee, can augment the soldier's normal nervous system response. Though the human nervous system is amazingly fast, it is not fast enough to allow for the muscular adjustments needed to deal with positions and situations where pain, swelling and fatigue become factors. The neuromuscular reflex system cannot respond quickly enough to deal with unanticipated, quickly applied, forces, which ultimately puts internal and external structures at risk of being injured. The reason the human nervous system is not fast enough to react is that the message the sensory system is sending from the knee has to travel the length of the body to the brain's cerebellum, be analyzed and processed, then sent to the motor cortex of the brain where the motor response is sent back down to the muscles supporting the knee. This relay system happens in a split second; but it is still not fast enough to yield the correct muscular adjustment to prevent injury. The end result can be an injured soldier. An electronic controller, in conjunction with a magnetorheological (MR) fluid shock system, or other fluid damper whose characteristics can be altered by way of computer command through an electromechanical interface, can sense and react within a couple of milliseconds; offering stability and assistance until the human response reaches the muscle. The motion of the knee and forces in the shocks are measured directly by the electronic controller. The electronic controller has the authority to dynamically adjust the level of support to suit the prevailing situation. Some embodiments of the present invention are able to deal with external influences, such as unseen changes in terrain during weight bearing activities, and the adverse effects of reduced muscular capabilities associated with prolonged exercise.

In a combat or battlefield situation, the more capabilities that our soldiers possess, the greater the likelihood of a successful mission will be. Some embodiments of the present invention can give our men and women in uniform the ability to push themselves harder and faster while reducing the occurrence of knee joint failure. In many circumstances, this "competitive and technological" advantage can mean the difference between a mission's success and its failure.

Some embodiments of the present invention can provide the United States Military with many economic advantages. With the knee brace in use during training and combat situations the soldier will be decreasing his or her chance of a knee injury. The prevention of injury and quicker recovery time from an uneventful mission, as relates to medical issues, will allow the military to save money on future rehabilitation costs and possibly on the number of trained soldiers deployed throughout the world. In the event of a knee injury occurring during a military or non-military endeavor, the bracing system may be able to facilitate a quicker rehabilitation time for the soldier. The reduction of treatment time will reduce the cost of the rehabilitation, and replacement of the soldier's duty with another soldier. There exists the possibility that a soldier may be able to return to combat duty when not at one hundred percent, with the brace allowing for normal knee function. Finally, the potential to use the brace as a training tool, to increase the strength of the knee prior to actual live combat missions, may allow for soldiers to perform above their normal, standard levels.

The present invention provides a superior bracing device to deal with the unique issues presented with respect to protecting body joints to avoid injury or to aid in recovery from an injury. In one embodiment, the brace includes a particular four bar linkage, described elsewhere, that simulates the non-linear motion of the biological knee joint. Comparable linkages which mimic other joint movements, such as the elbow or ankle, can also be used, as will be well appreciated by those skilled in the art. A hydraulic cylinder provides for accurately controlled motion, and a servo-valve or like device, in concert with a 1000-psi or other suitable pump, provides the controlled flow of fluid to and from the hydraulic cylinder with rapid response time. Position sensors monitor the motion of the linkage and cylinder, and strain gauges measure the very small extensions and compressions that occur, yielding an accurate measure of the force acting on the bracing device, and allowing fine and quick tuning of the bracing device in response to applied stresses. A gyrometer is coupled with the bracing device to provide artificial balance control. A data acquisition device gathers the data from the sensors and can store the information on a removable memory device, from which the data can be downloaded for analysis. A central processing unit is provided to apply control routines to the bracing device.

Figure 16:
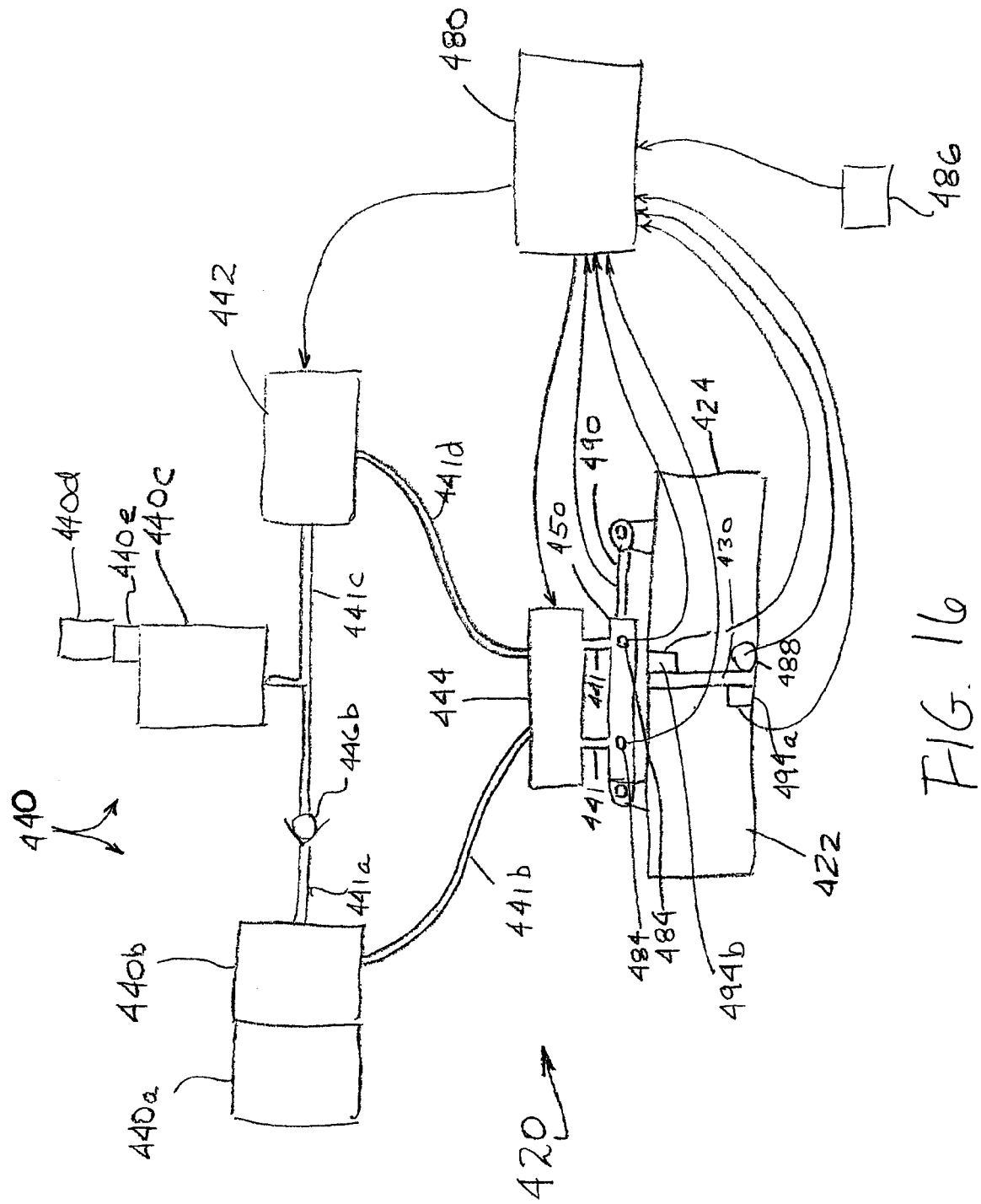
FIG. 16 is a schematic representation of an orthotic device according to another embodiment of the present invention.

FIG. 16 is a schematic representation of a powered orthotic device 420 according to another embodiment of the present invention. System 420 includes a pair of limb attachments 422 and 424 which grasp the limbs of an animal on opposite sides of a joint, such as a knee joint. The upper and lower attachments 422 and 424 are interconnected by a pair of exterior and interior joint linkages 430 and a force modifying apparatus 450. Some embodiments further include a second force modifying apparatus on the other side of the joint.

Apparatus 450 is adapted and configured to provide both passive resistance of varying degree (as an adjustable damper), and also able to provide force to push or pull one side of a joint relative to the other side of the joint (for example, the upper leg relative to the lower leg, or the lower leg relative to the foot). Pressure to enable apparatus 450 to function as an actuator comes from power assembly 440. Assembly 440 includes a pump 440b which provides up to about 1000 psig at the hydraulic connection 441a at the pump output. Motive force for pump 440b comes from a battery and motor 440a. The duty cycle of the pump is minimized by a source of pressure 440d such as a CO2 cartridge which acts through a pressure regulator 440e to maintain the supply pressure on one side of an accumulator 440c. Motive requirement of the pump are also minimized in some embodiments of the present invention by inclusion of a pressure recovery hydraulic circuit which boosts the pressure at the hydraulic connection 441b to the pump input from fluid being dumped from the non-working side of apparatus 450.

Pressure in conduit 441c is provided to a servo valve 442 (such as a one-stage or two-stage Moog © valve), which provides a modified pressure at valve output 441*d* based on a control signal received from controller 480. This control pressure is subsequently provided to a routing valve 444, which is under the control of computer 480 and can route the high pressure to either side of the piston 450*a* of force modifying apparatus 450. Further, computer 480 can command valve 444 to route fluid between chambers 450*b* and 450*c*, in which case apparatus 450 acts as a damper.

System 420 also include a single plane gyrometer 486 attached to the user, such as on the back. In a manner similar to control of a Segway © 2 wheeled personal transportation device, the user moves his back forward or aft to provide forward or aft command signals, respectively, to computer 480. Computer 480 determines what pressure to apply by taking into account the state of the joint from various sensors. These sensors includes piezoelectric load cells 494*a* and 494*b*, which detect the amount of pressure being applied at the contact interface of the flexion and extension stops, 432*a*/434*a* (flexion) and 432*b*/434*b* (extension), respectively. Additional state information is received from the actuator Hall effect sensor 490 of shaft 450*f*. Closed loop feedback of the pressures of apparatus 450 are proved by a pair of pressure sensors 484, one each in fluid communication with chambers 450*b* and 450*c*.

The present invention also contemplates those embodiments in which the system provides powered assistance to multiple joints, such as a leg orthotic device which would include hip, upper leg, lower leg, and foot attachments, each attachment interconnected to the adjacent attachment by one or more separate force modifying devices and joint linkages.

Figure 17:
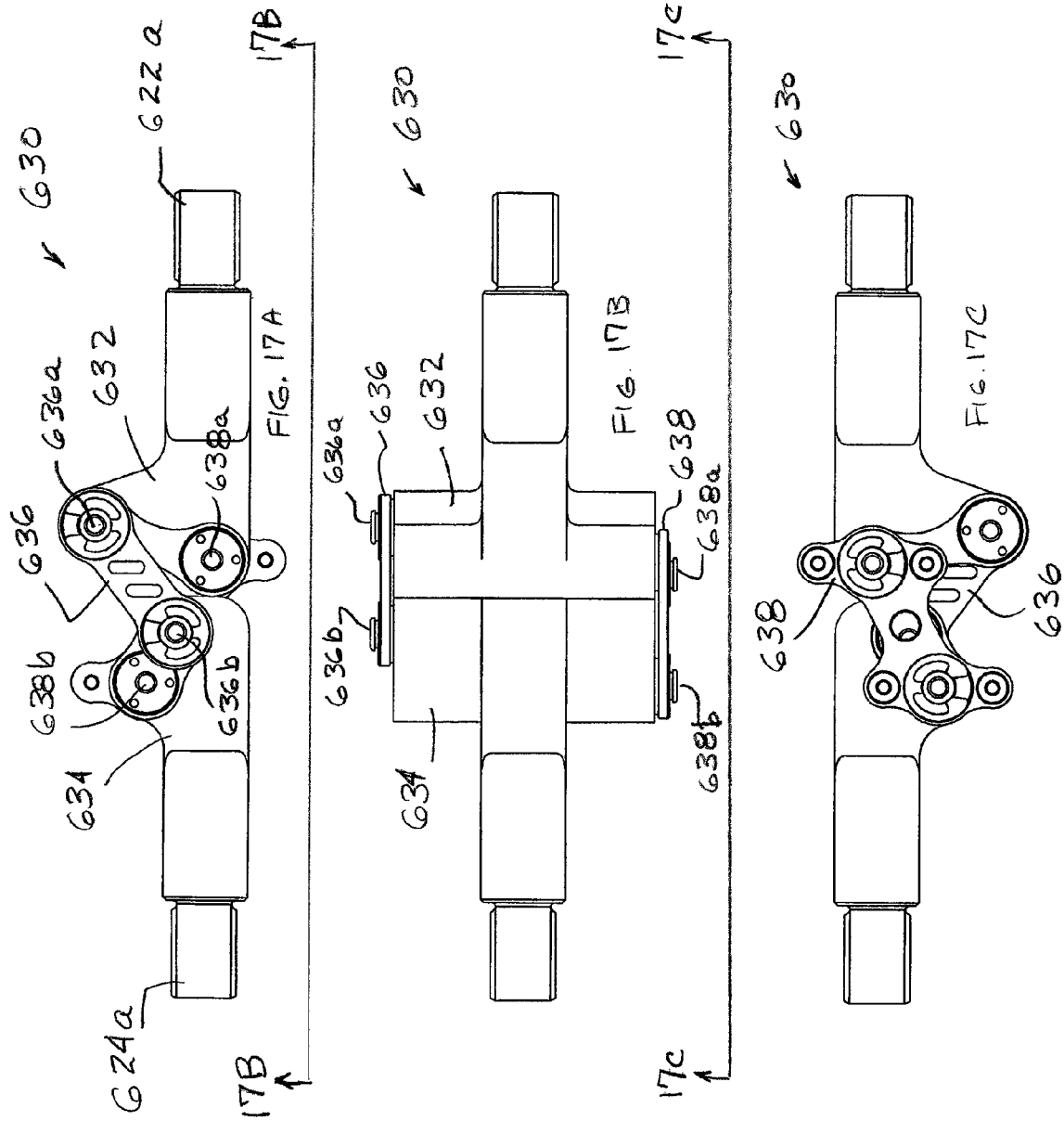
FIG. 17A is a side view of a prosthetic hinge according to another embodiment of the present invention.
FIG. 17B is a view of the hinge of FIG. 19A as taken along lines 19B-19B of FIG. 19A.
FIG. 17C is a view of the hinge of FIG. 19B as taken along lines 19C-19C of FIG. 19B.

FIGS. 17A, 17B, and 17C show orthogonal views of a prosthetic joint assembly 630 according to another embodiment of the present invention. Other aspects of a prosthetic knee unit can be found in U.S. Pat. No. 6,902,585, issued Jun. 7, 2005 to Hikichi; and U.S. Pat. No. 6,911,050, issued Jun. 28, 2005 to Molino, et al.; both of which are incorporated herein by reference. As can be seen best in FIGS. 17A and 17C, joint assembly 630 includes an upper leg attachment 622 and a lower leg attachment 624 kinematically coupled together by a four bar linkage. The upper link 632 and lower link 634 of the four bar linkage are rigidly connected to attachments 622 and 624, respectively, and in some embodiments are integral with attachment 622 and 624, respectively. A pair of interconnecting links 636 and 638 are pivotally coupled at either end to upper links 632 and 634. Prosthetic joint assembly 630 has substantially the same geometry and kinematic motion as the orthotic joint assembly 30 shown previously, although other embodiments can have different geometry and kinematic motion.

Rigid bodies 622*a* and 624*a* of the upper and lower leg attachments include features for incorporating prosthetic joint 630 into a prosthetic limb. For example, upper rigid body 622*a* can include features on the end for coupling into the upper leg of an animal. The end of the lower rigid body 624*a* can include features for coupling of the joint into a prosthetic lower limb. As can be seen best in FIG. 17B, prosthetic joint 630 can include widened pivot joints 636*a*, 636*b*, 638*a* and 638*b* for improved lateral stability, and also for increased bearing area and lower bearing stresses. In some embodiments, one or all of these pivot joints are internally supported by roller bearings or ball bearings.

Figure 18:
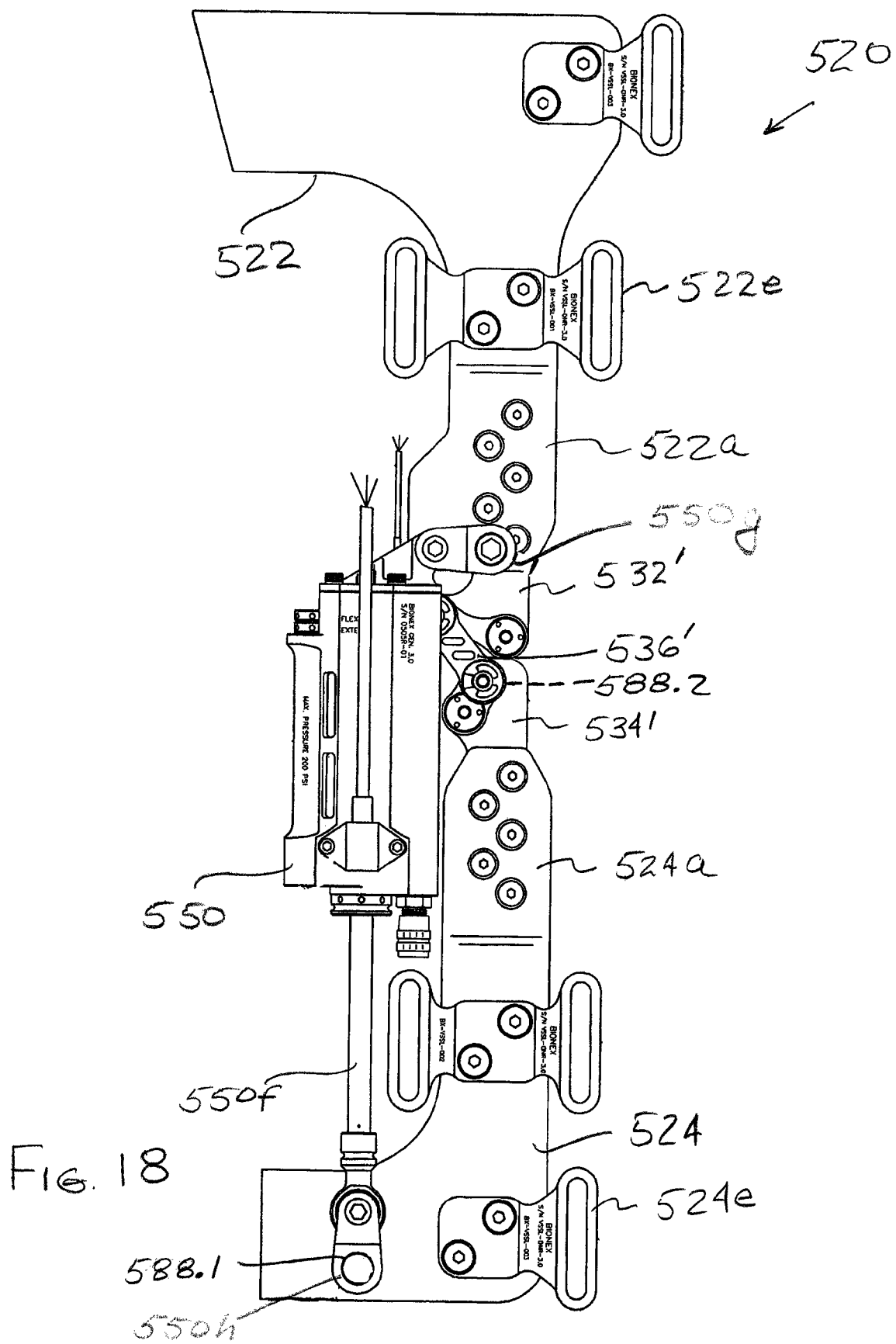
FIG. 18 is a scaled, side-elevational view of an apparatus according to another embodiment of the present invention.

FIG. 18 is a scaled side elevational view of an orthotic knee brace 520 according to another embodiment of the present invention.

Orthotic knee brace 520 is substantially the same as braces 20, 120, 220, and 420, except as shown and described herein. In one embodiment, knee brace 520 includes a sensor for measuring rapid movement of the lower limb portion of the knee brace to protect the user from inputs that would otherwise be damaging to the knee. For example, a person parachuting receives a sudden, flexing input to the knee joint during landing. As another example, persons standing in a boat receive sudden flexing inputs to the knee when the boat is pushed upward by wave motion.

In some embodiments, knee brace 520 includes a sensor 588.1 which measures the angular position of one link of the four bar linkage relative to another link of the four bar linkage. Referring to FIG. 5B, in one embodiment the sensor 588.2 measures the angular relationship or angular velocity of link 532' relative to interconnecting link 538. As noted in FIG. 19 this angle changes approximately linearly with the knee joint angle. In some embodiments, sensor 588.2 is a potentiometer or digital encoder. In yet other embodiments, sensor 588.2 includes a Hall Effect sensor such as that shown in U.S. Patent Application Publication 2002/0143279 (to Porier et al.) published Oct. 3, 2002, and incorporated herein by reference. In yet other embodiments, sensor 588.1 is an accelerometer (uniaxial, biaxial, or triaxial) attached to lower leg attachment 524.

Although angular position and acceleration sensors have been shown and described, it is appreciated that the sensor can be of any type which permits inference of sudden movement of the knee joint. In those embodiments in which the user is falling toward ground (such as a parachutist), the sensor could also be an altimeter such as a ground proximity radar sensor which supplies a signal corresponding to impending impact.

Signals from sensor 588 are sent to an electronic controller 580 which uses the signal to calculate a value corresponding to the rate at which the knee is flexing. This calculated value is compared to a predetermined limit which is established for protection of the knee from sudden, jarring, impact loads. However, in other embodiments the predetermined limit can be established based on other considerations, including, for example, rehabilitation.

If the sensor senses a haptic event that could suddenly flex the knee joint and subsequently overload the knee, then an algorithm within the electronic controller can take action to momentarily increase the damping characteristics of the damper. As one example, a user of the brace operates a high speed boat which encounters significant waves. As the bottom of the boat rises up toward the user, an acceleration is imparted from the lower leg which could overstress the knee joint. The electronic controller compares the sensed input, such as an acceleration of the lower leg attachments or a change in relative angular position between two of the links, and compares the measured motion to a predetermined, threshold limit for motion. Preferably, this limit is set to avoid overstressing of the knee. If this limit is exceeded, the electronic controller actuates the damper to momentarily increase its resistive force. As a result of these change in damping characteristics, some of the load which would otherwise pass through the knee joint instead bypasses the knee joint and is applied to the soft tissue of the upper leg, and also dissipated as heat within the damping fluid.

In one embodiment, knee brace 520 includes upper and lower leg attachment rigid bodies 22*a* and 24*a*, respectively, which are fabricated from aluminum, such as 6061-T6. Damper 550 is pivotally coupled by an upper clevis 550*g* and lower clevis 550*h* which are preferably fabricated from titanium, such as 6Al-4V titanium, and including a surface treatment of titanium carbo nitride. The various attachment loops 524*e* are preferably fabricated from aluminum such as 7075-T6 with a surface that has been anodized with a sulfuric acid solution. Although various specific coatings and material have been shown and described, it is understood that they are by way of example only, and are not limiting to any embodiment of the present invention.

In some embodiments knee brace 520 is adapted and configured to support a knee during flexion, especially for users experiencing hard "slamming" events, such as during high speed boating and parachuting. The upper and lower rigid bodies 522*a* and 524*a* are adapted and configured to include rigid partial hoops which couple to the rear thigh and rear calf, respectively, of a user. These rigid partial hoop sections 522*a* and 524*a* are partly open toward the anterior of the respective limb, with this open area being coupled to the limb by way of flexible straps. By placing the rigid portions toward the side of the limb for resistance to flexing (i.e. the posterior side for a leg), it is possible to provide a better load path into the soft tissue of the limb. However, the present invention also contemplates those embodiments in which the rigid portions are on the front side of the limbs, and on alternate sides of the limbs.

Figure 19:
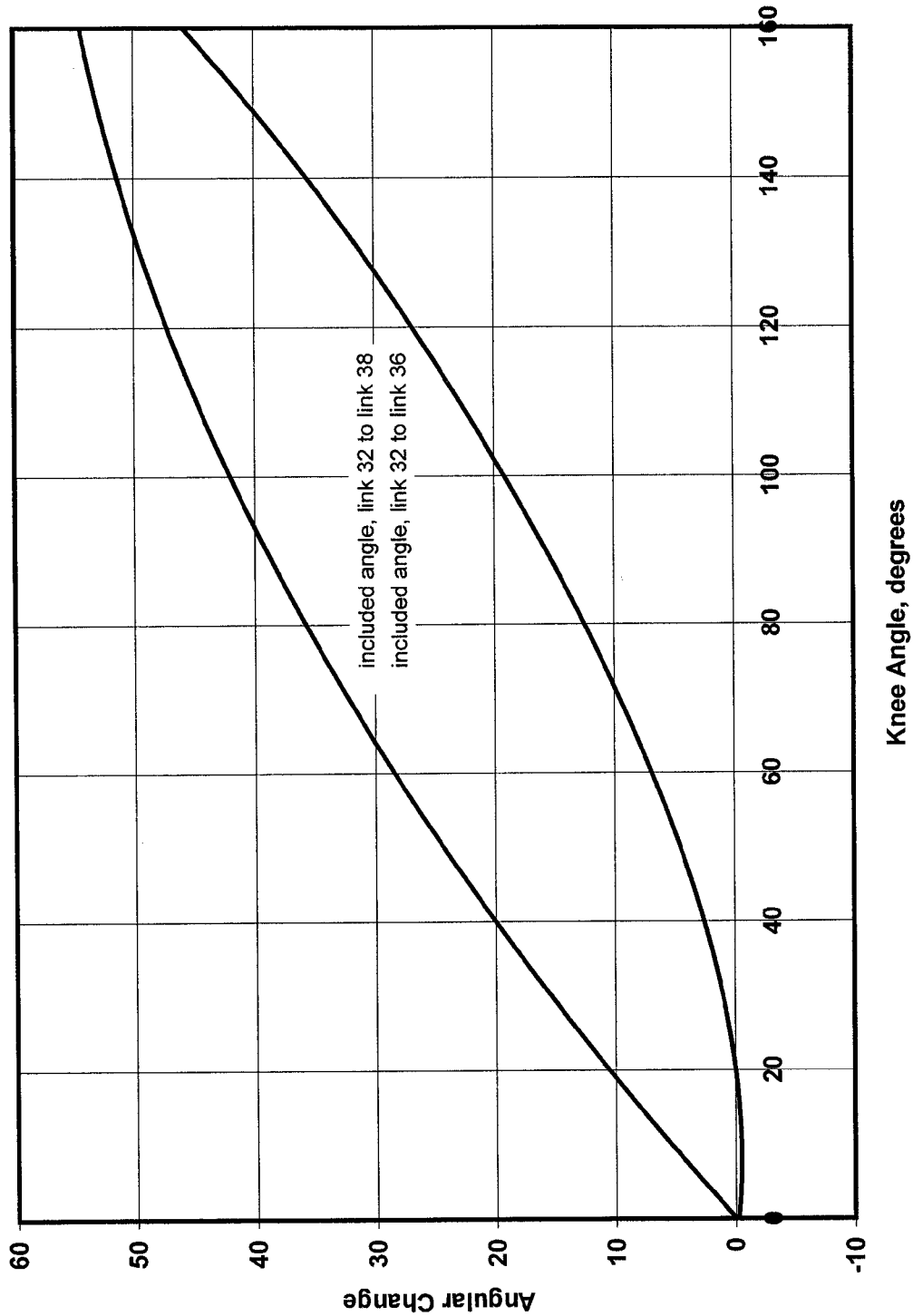
FIG. 19 is a graph describing the angular operation of a linkage according to one embodiment of the present invention.

FIG. 19 is a graph depicting the angular relationship between the angle of the knee and the angular change in the two interconnecting links 538 and 536 relative to the femoral link. Referring to FIG. 5B, the top line represents the change in the included angle between links 532 and 538 relative to the knee angle from full extension (0 degrees) toward flexion. Referring to FIG. 5C, the bottom curve is the included angle between femoral link 532 and interconnecting link 536 as a function of knee angle.

The bottom line of FIG. 19 shows that the angular relationship between link 532 and link 536 shows vary little change for the first 20 degrees of motion from full extension toward flexion. In contrast, the included angle between links 532 and 538 changes approximately linearly for these same first 20 degrees of movement from full extension.

As the knee continues to flex toward higher degrees of flexion, this relationship changes. For example, from knee angles from 140 to 160 degrees, the included angle between link 532 and link 538 only changes by about 3 degrees, whereas the included angle between link 532 and link 536 changes by about 10 degrees.

Figure 20:
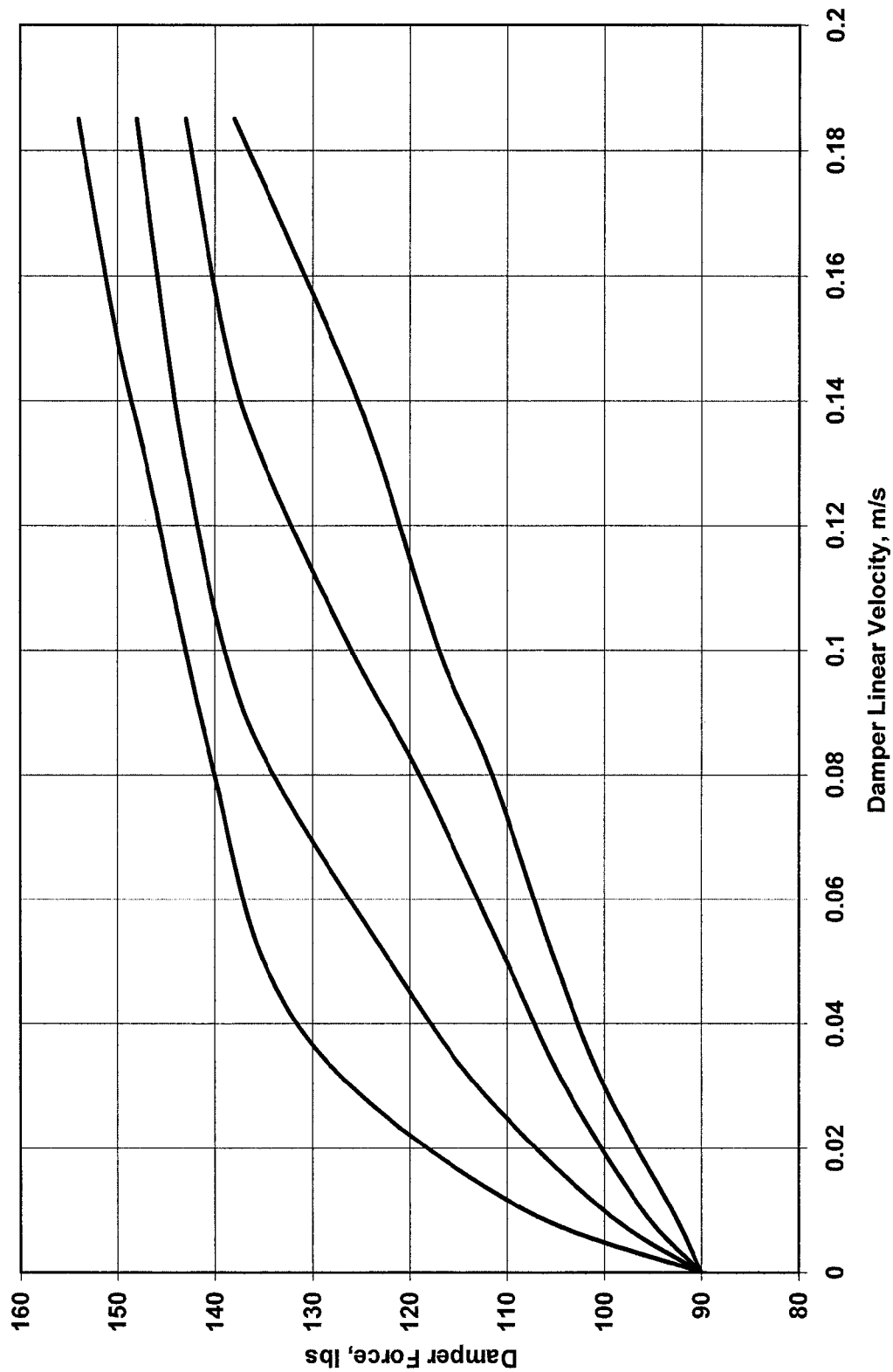
FIG. 20 is a graph depicting the damping force characteristics of a damper according to one embodiment of the present invention.

FIG. 20 is a plot of the resistive force applied by a force modifying apparatus 550 according to one embodiment of the present invention. In the depicted embodiment, the force modifying apparatus includes an adjustable restriction for modification of the resistive force during damper compression (i.e. knee flexion). Each of the four curves of FIG. 20 depicts the resistive (damping) force provided as a function of the linear velocity of the damper shaft for each of four different orifice adjustments. In yet other embodiments of the present invention, the damper includes an internal blow-off feature which limits the amount of resistive force which can be provided. As shown in FIG. 20, this blow-off feature operated at about 140 pounds.

As is shown best in the leftmost curve of FIG. 20, damper 550 exhibits at least two damping characteristics: (1) a first, steeper characteristic at lower velocities, and (2) a shallower damping characteristic for resistive forces of approximately 140 pounds. This force-limiting aspect of damper 550 thereby limits the amount of force that will be transferred from the lower attachment member to the upper attachment member. In those embodiments in which damper 550 is part of an orthotic knee brace, this limits the load being applied to soft tissue. In some embodiments, the internal blow-off feature is a pressurizing valve which unseats itself at an internal pressure corresponding to the desired force limit. It is understood that the present invention contemplates any type of pressure or force limiting system, such as a spring loaded check ball, a flapper valve, and also those systems in which the forces are measured (such as with a load cell) and limited by a computer via electrical actuation.

Figure 21:
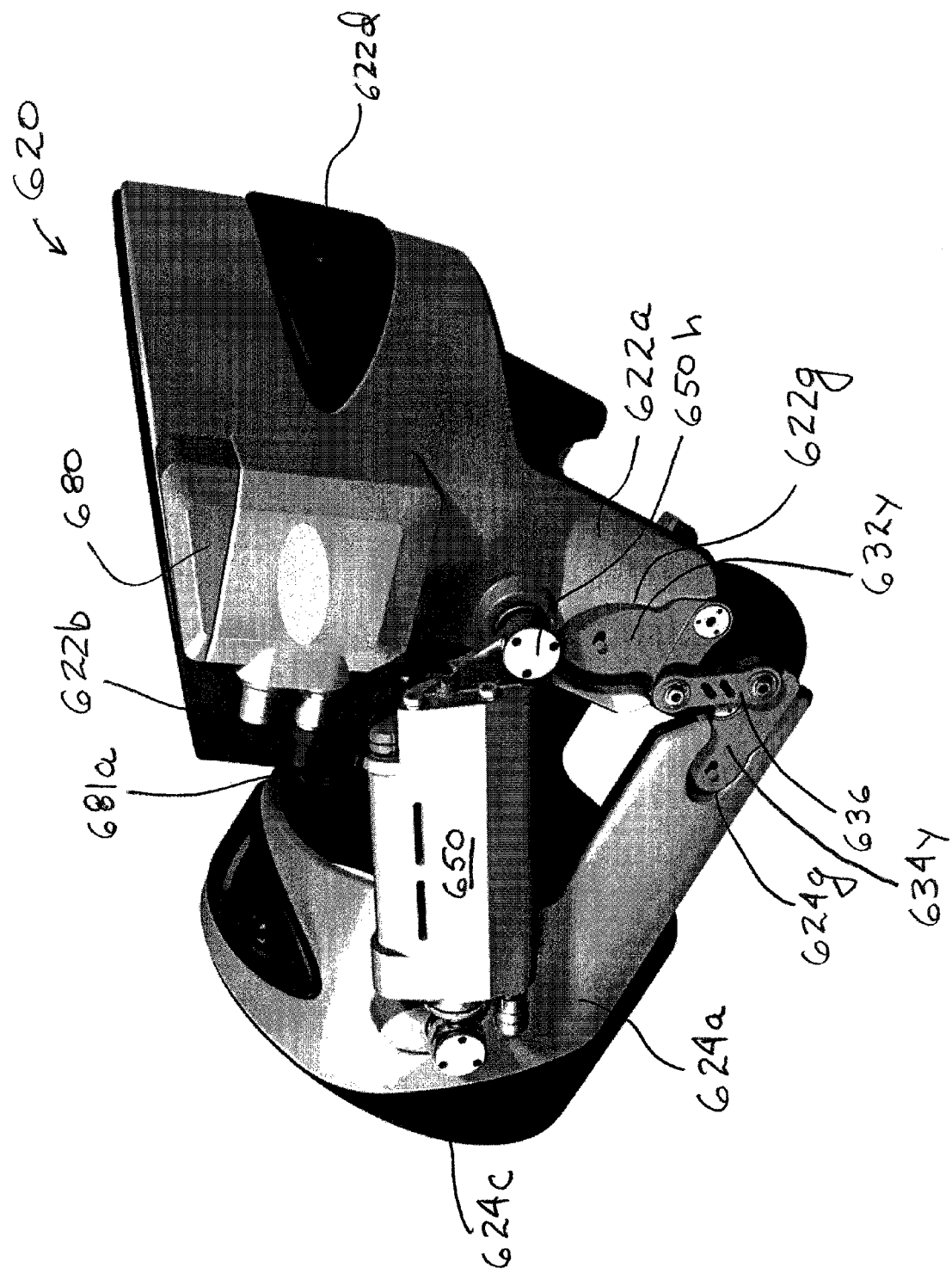
FIG. 21 is a top, side, perspective view of an apparatus according to another embodiment of the present invention.

The knee braces shown in FIGS. 1, 9, 13, and 18 include dampers which are pivotally connected to the brace in order to provide sufficient velocity to the damper (i.e., relative velocity between the moving damper elements). As best seen in FIG. 18, one end of damper 550 is coupled by a clevis 550*g* at a location proximate to the pivotal connections between the upper and lower leg attachments 522 and 524, respectively. The other end of damper 550 is coupled by a clevis 550*h* to the rigid body 524*a* in a region proximate to the rigid partial hoop supporting the posterior of the calf. Therefore, as upper and lower leg attachments 522 and 524 pivot relative to each other, shaft 550*f* has a sufficient velocity relevant to damper body 550*e* that a sufficient resistive torque is applied. It has been noted in some experiments that the peak moments on the knee during slamming events can be in excess of 400 Newton-meters FIG. 21 is a top, side, perspective view of an orthotic brace according to one embodiment of the present invention, and shown in a flexed position (similar to FIG. 9). Knee brace 620 includes several features that improve the packaging and durability of an orthotic knee brace. Controller 680 is placed to a side of upper rigid body 622*a*. Such placement on the same side of the brace as damper 650 allows for a shorter electrical interconnection to damper 650 and other sensors. Further, this laterally outward placement decreases the forward-projecting portion of the knee brace space envelope.

In some embodiments, upper rigid member 622*a* and lower rigid member 624*a* are fabricated from a lightweight, moldable material such as a carbon composite material. In some embodiments, the portions of these rigid bodies proximal to the four bar linkage include form-fitting recessed pockets 622*g* and 624*g*, respectively. As can be seen in FIG. 21, a rigid upper link 632*y* has a shape complementary to pocket 622*g*. The shapes of this load distribution link 632*y* and pocket 622*g* are chosen to provide efficient distribution of loads into rigid member 622*a*. Likewise, rigid member 624*a* includes a pocket 624*g* which fits closely around a load distribution link 634*y*. In some embodiments, load distribution links 632*y* and 634*y* are fabricated from steel or titanium.

Some embodiments of the present invention include of a joint corresponding to a human knee joint. These embodiments can include a femoral member, a tibial member, a first link pivotally connected by a first pivot joint to a femoral member and pivotally connected by a second pivot joint to a tibial member, the first link having a first length from the center of the first pivot joint to the center of the second pivot joint, and the second link pivotally connected by a third pivot joint to the femoral member and pivotally connected by a fourth pivot joint to the tibial member, the second link having a second length from the center of the third pivot joint to the center of the fourth pivot joint. The femoral member is pivotal relative to the tibial member from an extended position to a flexed position, the first pivot joint being spaced apart from the third pivot joint by a first distance, the second pivot joint being spaced apart from the fourth pivot joint by a second distance, and the first length is greater than or about equal to the second length, the second length is greater than or about equal to the first distance, and the first distance is greater than the second distance.

Other embodiments can include a joint corresponding to a human joint. This knee joint further includes a femoral member, a tibial member, a first link having two ends and pivotally connected at a first end to the femoral member and pivotally connected at the second end to the tibial member, a second link having two ends and pivotally connected at a third end to the femoral member and pivotally connected at the fourth end to the tibial member. The femoral member is pivotal relative to the tibial member from an extended position to a flexed position, the first end being spaced apart from the third end by a first distance, the second end being spaced apart from the fourth end by a second distance, and the first distance is greater than the second distance.

Still other embodiments include a joint corresponding to a human knee joint. These embodiments include a femoral member, a tibial member, a first link having two ends and pivotally connected at a first end to the femoral member and pivotally connected at the second end to the tibial member, and a second link having two ends and pivotally connected at a third end to the femoral member and pivotally connected at the fourth end to the tibial member. The femoral member is pivotal relative to the tibial member from extension to flexion within a range of positions, the first and second links being adapted and configured such that the first end, second end, and fourth end are generally aligned when the joint is at a position corresponding to full extension of a human knee joint.

Other embodiments include a method for rehabilitating an animal joint. This joint provides a first limb attachment member pivotally coupled to a second limb attachment member, an electrically-actuatable resistive force device interconnecting the first limb and second limb attachment members, an electronic controller being operably connected to the resistive force device, and a sensor in electrical communication with the controller. The embodiment further includes inferring a force applied between the force device and one of the limb attachment members with the sensor and modifying the resistive force characteristics of the resistive force device by the controller and in response to the inferring.

Another embodiment of the present invention includes a method for protecting an animal joint comprising providing a first limb attachment member pivotally coupled to a second limb attachment member, an electrically-actuatable resistive force device interconnecting the first limb and second limb attachment members, an electronic controller operably connected to the force modifying device, and a sensor in electrical communication with the controller. The embodiment further includes sensing flexing of the first limb attachment member toward the second attachment member by the sensor, calculating with the controller a value corresponding to the rate of flexing, comparing the value to a predetermined flexure rate limit, and increasing the resistive force applied by the resistive force device if the value exceeds the rate limit.

Still other embodiments include a joint for replacing a knee joint of an animal. The embodiments include a femoral attachment member for coupling to an upper leg, a tibial replacement member for replacing a removed lower leg, and a four bar linkage interconnecting the femoral attachment member and the tibial replacement member, the linkage including a first link rigidly attached to the femoral attachment member, a second link rigidly attached to the tibial replacement member, a third link pivotally interconnecting the first link and the second link, and a fourth link pivotally interconnecting the first link and second link, each of the pivotal interconnections being spaced apart from all other pivotal interconnections.

Other embodiments of the present invention include a brace for a joint between two limbs of an animal, comprising a first attachment member for coupling to the exterior of the first limb, the first member including a first rigid portion positioned at the posterior of the first limb; a second attachment member for coupling to the exterior of the second limb, the second member including a second rigid portion positioned at the posterior of the second limb, the second rigid portion being pivotally connected to said first rigid portion; and a damper for resisting the pivotal motion of the first rigid portion relative to the motion of the second rigid portion.

The many embodiments discussed, shown, and inferable from this document are examples, and are not limiting. It is recognized that the various embodiments shown, discussed, and inferred from this document include numerous variations.

Some of these variations include, as single dependencies, successive dependencies, or multiple dependencies, that: the fourth end is aligned at a position intermediate of the first end and the second end; the third end is located to the rear of the second end; there is an upper leg member for external coupling to a human thigh, a lower leg member for external coupling to a human calf, wherein the femoral member is attached to the upper leg member and the tibial member is attached to the lower leg member; and the upper leg member includes an upper strap and an upper rigid body shaped at least in part for contact with a thigh, a lower strap and a lower rigid body shaped at least in part for contact with a calf, the femoral member being rigidly attached to the upper rigid body and the tibial member being rigidly coupled to the lower rigid body.

Some of these variations include, as single dependencies, successive dependencies, or multiple dependencies, that: the first link and second link are coupled by pivots joints that permit one dimensional rotation only; and the first end is spaced apart from the third end by a first distance, the second end is spaced apart from the fourth end by a second distance, and the first distance is at least about 50% greater than the second distance.

Some of these variations include, as single dependencies, successive dependencies, or multiple dependencies, that: there is a damper having two elements movable relative to one another, the damper requiring a damping force for movement of one element relative to the other element, one the damper element being coupled to the femoral member, the other damper element being coupled to the tibial element; one damper element translates relative to the other damper element; and the damper element rotates relative to the other damper element in a direction generally parallel to the pivoting of the femoral member relative to the tibial member.

Some of these variations include, as single dependencies, successive dependencies, or multiple dependencies, that: the first distance is at least about 50% greater than the second distance; the first distance is at least about twice than the second distance; the first length is greater than the second length, the second length is greater than the first distance, and the first distance is greater than the second distance; and the first length is more than double the second distance.

Some of these variations include, as single dependencies, successive dependencies, or multiple dependencies, that: at least one of the first pivot joint, second pivot joint, third pivot joint, or the fourth pivot joint is constrained to pivoting about a single axis; at least two of the first pivot joint, second pivot joint, third pivot joint, or fourth pivot joint is constrained to pivoting about a single axis; each of the first pivot joint, second pivot joint, third pivot joint, or fourth pivot joint is constrained to pivoting about a single axis; members are flat and planer where pivotally connected having 2 sides, one on one side, the other on the other; and the four bar linkage consists of four links that are coupled by pivots joints that permit pivoting only.

Some of these variations include, as single dependencies, successive dependencies, or multiple dependencies, that: the joint is a prosthetic joint for replacing a human knee joint, and the femoral member is coupled to an upper portion of a leg; and the joint is an orthotic joint for supporting a human knee joint, and the femoral member is externally coupled to an upper portion of a leg, and the tibial member is externally coupled to a lower portion of a leg.

Some of these variations include, as single dependencies, successive dependencies, or multiple dependencies, that: the four bar linkage permits pivoting of the first attachment member relative to the second attachment member from a flexed position to an extended position, and the damper provides greater resistance to movement from the extended position toward the flexed position than from the flexed position toward the extended position; and the first attachment member couples to an upper leg, the second attachment member couples to a lower leg.

Some of these variations include, as single dependencies, successive dependencies, or multiple dependencies, that: a first link of the four bar linkage is pivotally coupled at one end to the first attachment member and pivotally coupled at the other end to the second attachment member, a second link of the four bar linkage is pivotally coupled at one end to the first attachment member and pivotally coupled at the other end to the second attachment member, the first link having a first length between pivotal couplings, the second link having a second length between pivotal couplings, the first length being about the same as the second length, the first link not being parallel to the second link.

Some of these variations include, as single dependencies, successive dependencies, or multiple dependencies, that: the four bar linkage includes a first link pivotally coupled at a first end to the first attachment member and pivotally coupled at a second end to the second attachment member, a second link pivotally coupled at a third end to the first attachment member and pivotally coupled at a fourth end to the second attachment member, the first pivot joint being spaced apart from the third pivot joint by a first distance, the second pivot joint being spaced apart from the fourth pivot joint by a second distance, and the first distance is greater than the second distance.

Some of these variations include, as single dependencies, successive dependencies, or multiple dependencies, that: the four bar linkage includes a first link pivotally coupled at a first end to the first attachment member and pivotally coupled at a second end to the second attachment member, a second link pivotally coupled at a third end to the first attachment member and pivotally coupled at a fourth end to the second attachment member, the first attachment member having a side adjacent to the limb and a side away from the limb, and the first link is pivotally coupled to the first attachment member and the second attachment member on the side adjacent to the limb, and the second link is pivotally coupled to the first attachment member and the second attachment member on the side away from the limb.

Some of these variations include, as single dependencies, successive dependencies, or multiple dependencies, that: the four bar linkage consists of four links that are coupled by pivots joints that permit pivoting only; the four bar linkage is a first four bar linkage, and which further comprises a third attachment member for coupling around the exterior of the first limb, a fourth attachment member for coupling around the exterior of the second limb, and a second four bar linkage connecting third first member to the fourth member, the second four bar linkage having the same kinematics as the first four bar linkage; and the second four bar linkage is a mirror image of the first four bar linkage.

Some of these variations include, as single dependencies, successive dependencies, or multiple dependencies, further includes a four bar linkage for determining the kinematics of said first member relative to the motion of said second member, said linkage including a first separable link pivotally connected to a first extension of said first rigid portion and pivotally connected to a second extension of said second rigid portion, and a second separable link pivotally connected to said first extension of said first rigid portion and pivotally connected to said second extension of said second rigid portion, said first extension including a third link, said second extension inducing a fourth link; the first rigid portion has a partial hoop shape open across the anterior of the first limb, said second rigid portion has a partial hoop shape open across the anterior of the second limb, said first attachment member includes a first flexible strap attachable to said first rigid potion, and said second attachment member includes a second flexible strap attachable to said second rigid potion; and the damper has a first resistive force characteristic corresponding to flexion of the limb and a second resistive force characteristic corresponding to extension of the limb, the first characteristic being different than the second characteristic, said damper generally applying more resistive force in flexion than in extension.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A brace for a joint between two limbs of an animal, comprising:
    a first attachment member for coupling to the exterior of the first limb;
    a second attachment member for coupling to the exterior of the second limb;
    a four bar linkage for determining the kinematics of the first member relative to the motion of the second member; and
    a damper for resisting the pivotal motion of the first member relative to the motion of the second member;
    wherein said first attachment member includes a rigid portion defining a pocket having a first shape, said second attachment member includes a rigid portion defining a pocket having a second shape, and said four bar linkage includes a first link having a peripheral shape corresponding to the shape of said first pocket, a second link having a peripheral shape corresponding to the shape of said second pocket, a third link pivotally connected to said first link and said second link, and a fourth link pivotally connected to said first link and said second link.

2. The brace of claim 1 wherein said damper is a fluid damper having two elements movable relative to one another, said damper providing a damping force for resisting movement of one element relative to the other element, one said damper element being coupled to said first member, the other said damper element being coupled to said second element.

3. The brace of claim 2 wherein one said damper elements translates relative to the other said damper element.

4. The brace of claim 2 wherein one said damper element is pivotally coupled to the first member at a location proximal to said four bar linkage, and said other damper element is pivotally coupled to said second attachment member at a location distal from said four bar linkage.

5. The brace of claim 1 wherein said four bar linkage permits pivoting of said first attachment member relative to said second attachment member from a flexed position to an extended position, and said damper provides greater resistance to movement from the extended position toward the flexed position than from the flexed position toward the extended position.

6. The brace of claim 1 wherein a first link of said four bar linkage is pivotally coupled at one end to said first attachment member and pivotally coupled at the other end to said second attachment member, a second link of said four bar linkage is pivotally coupled at one end to said first attachment member and pivotally coupled at the other end to said second attachment member, said first link having a first length between pivotal couplings, said second link having a second length between pivotal couplings, the first length being about the same as the second length, the first link not being parallel to said second link.

7. The brace of claim 1 wherein said damper is a fluid damper, said damper including an internal valve for limiting the maximum fluid pressure within said damper.

8. The brace of claim 1 wherein said four bar linkage includes a first link pivotally coupled at a first pivot joint to said first attachment member and pivotally coupled at a second pivot joint to said second attachment member, a second link pivotally coupled at a third pivot joint to said first attachment member and pivotally coupled at a fourth pivot joint to said second attachment member, said first pivot joint being spaced apart from said third pivot joint by a first distance, said second pivot joint being spaced apart from said fourth pivot joint by a second distance, and the first distance is greater than the second distance.

9. The brace of claim 1 wherein said first attachment member couples to a thigh, said second attachment member couples to a calf, said first attachment member includes a rigid, partial hoop shape positioned at the posterior of the first limb and open across the anterior of the first limb, said second attachment member includes a rigid, partial hoop shape positioned at the posterior of the second limb and open across the anterior of the second limb.

10. A brace for a joint between two limbs of an animal, comprising:
    a first attachment member for coupling to the exterior of the first limb;
    a second attachment member for coupling to the exterior of the second limb;
    a four bar linkage for determining the kinematics of the first member relative to the motion of the second member; and
    a damper for resisting the pivotal motion of the first member relative to the motion of the second member;
    wherein said first attachment member includes a rigid portion defining a pocket having a first shape, said second attachment member includes a rigid portion defining a pocket having a second shape, and said four bar linkage includes a first link having a peripheral shape corresponding to the shape of said first pocket, a second link having a peripheral shape corresponding to the shape of said second pocket, a third link pivotally connected to said first link and said second link, and a fourth link pivotally connected to said first link and said second link; and
    wherein said first attachment member couples to a thigh, said second attachment member couples to a calf, said first attachment member includes a rigid, partial hoop shape positioned at the posterior of the first limb and open across the anterior of the first limb, said second attachment member includes a rigid, partial hoop shape positioned at the posterior of the second limb and open across the anterior of the second limb.

11. The brace of claim 10 wherein said damper is a fluid damper having two elements movable relative to one another, said damper providing a damping force for resisting movement of one fluid damper element relative to the other fluid damper element, one said fluid damper element being coupled to said first member, the other said fluid damper element being coupled to said second element.

12. The brace of claim 11 wherein one said fluid damper elements translates relative to the other said fluid damper element.

13. The brace of claim 11 wherein one said fluid damper element is pivotally coupled to the first member at a location proximal to said four bar linkage, and said other fluid damper element is pivotally coupled to said second attachment member at a location distal from said four bar linkage.

14. The brace of claim 10 wherein said four bar linkage permits pivoting of said first attachment member relative to said second attachment member from a flexed position to an extended position, and said damper provides greater resistance to movement from the extended position toward the flexed position than from the flexed position toward the extended position.

15. The brace of claim 10 wherein a first link of said four bar linkage is pivotally coupled at one end to said first attachment member and pivotally coupled at the other end to said second attachment member, a second link of said four bar linkage is pivotally coupled at one end to said first attachment member and pivotally coupled at the other end to said second attachment member, said first link having a first length between pivotal couplings, said second link having a second length between pivotal couplings, the first length being about the same as the second length, the first link not being parallel to said second link.

16. The brace of claim 10 wherein said damper is a fluid damper, said damper including an internal valve for limiting the maximum fluid pressure within said damper.

17. The brace of claim 10 wherein said four bar linkage includes a first link pivotally coupled at a first pivot joint to said first attachment member and pivotally coupled at a second pivot joint to said second attachment member, a second link pivotally coupled at a third pivot joint to said first attachment member and pivotally coupled at a fourth pivot joint to said second attachment member, said first pivot joint being spaced apart from said third pivot joint by a first distance, said second pivot joint being spaced apart from said fourth pivot joint by a second distance, and the first distance is greater than the second distance.

18. A method for rehabilitating an animal joint, comprising:
    providing a brace for a joint between two limbs of an animal, comprising:
    a first limb attachment member for coupling to the exterior of the first limb;
    a second limb attachment member for coupling to the exterior of the second limb;
    a four bar linkage for determining the kinematics of the first limb attachment member relative to the motion of the second limb attachment member; and
    a damper for resisting the pivotal motion of the first limb attachment member relative to the motion of the second limb attachment member;
    wherein said first limb attachment member includes a rigid portion defining a pocket having a first shape, said second limb attachment member includes a rigid portion defining a pocket having a second shape, and said four bar linkage includes a first link having a peripheral shape corresponding to the shape of said first pocket, a second link having a peripheral shape corresponding to the shape of said second pocket, a third link pivotally connected to said first link and said second link, and a fourth link pivotally connected to said first link and said second link;

an electrically-actuatable resistive force device interconnecting the first limb and second limb attachment members, an electronic controller having memory and being operably connected to the resistive force device, and a sensor in electrical communication with the controller;

sensing movement of one of the limb attachment members with the sensor;

storing a history of the sensed movement in the memory; and modifying the resistive force characteristics of the resistive force device by the controller and in response to the history.

19. The method of claim 18 wherein the sensor provides a signal corresponding to the angular relationship of the first limb attachment member relative to the second limb attachment member, and said modifying is a function of the angular relationship.

20. The method of claim 18 wherein said modifying is in response to whether the joint is being extended or flexed.

21. The method of claim 18 wherein the resistive force device operates with magnetorheological fluid and said modifying is by altering the characteristics of the fluid in response to commands from the electronic controller.

22. An apparatus attached proximate to a joint between two limbs of an animal, comprising:

a first attachment member for coupling around the exterior of the first limb;

a second attachment member for coupling around the exterior of the second limb and pivotally connected to said first attachment member;

an electrically-actuatable resistive force device having a forcing characteristic which resists the motion of said first member relative to the motion of said second member, the forcing characteristic capable of being modified by an input command;

a sensor for sensing a parameter resulting from movement of one of said first member or said second member and producing a signal corresponding to the parameter;

an electronic controller operably connected to said resistive force device and receiving the signal, said controller providing the command in response to the signal;

a four bar linkage for determining the kinematic motion of said first member relative to the second member;

a first attachment member for coupling to the exterior of the first limb, said first member including a first rigid portion positioned at the posterior of the first limb; a second attachment member for coupling to the exterior of the second limb, said second member including a second rigid portion positioned at the posterior of the second limb, said second rigid portion being pivotally connected to said first rigid portion; and wherein said first rigid portion has a partial hoop shape open across the anterior of the first limb, said second rigid portion has a partial hoop shape open across the anterior of the second limb, said first attachment member includes a first flexible strap attachable to said first rigid portion, and said second attachment member includes a second flexible strap attachable to said second rigid potion.

23. The apparatus of claim 22 wherein said sensor is a load cell or an angular position sensor.

24. The apparatus of claim 22 wherein said force device operates with magnetorheological fluid.

* * * * *